(12) United States Patent
Berry et al.

(10) Patent No.: US 7,700,723 B2
(45) Date of Patent: Apr. 20, 2010

(54) POLYPEPTIDES AND ENCODING POLYNUCLEOTIDES FOR MICROBIAL PRODUCTION OF L-ASCORBIC ACID AND ASSOCIATED METHODS

(75) Inventors: Alan Berry, Manlius, NY (US); Connie Lee, Reykjavik (IS); Anne Françoise Mayer, Basel (CH); Masako Shinjoh, Kanagawa (JP)

(73) Assignee: DSM IP Assets B.V., Heerlen (NL)

( * ) Notice: Subject to any disclaimer, the term of this patent is extended or adjusted under 35 U.S.C. 154(b) by 480 days.

(21) Appl. No.: 10/567,763

(22) PCT Filed: Aug. 16, 2004

(86) PCT No.: PCT/CH2004/000511
§ 371 (c)(1),
(2), (4) Date: Jun. 9, 2006

(87) PCT Pub. No.: WO2005/017159
PCT Pub. Date: Feb. 24, 2005

(65) Prior Publication Data
US 2007/0184534 A1    Aug. 9, 2007

(30) Foreign Application Priority Data
Aug. 14, 2003  (EP) ................... 03017677

(51) Int. Cl.
*C07K 1/00* (2006.01)
(52) U.S. Cl. .................. 530/350; 530/300; 435/126; 514/12
(58) Field of Classification Search .............. None
See application file for complete search history.

(56) References Cited

FOREIGN PATENT DOCUMENTS

| EP | 0 911 415 | 4/1999 |
|---|---|---|
| EP | 0 922 759 | 6/1999 |
| WO | WO 97/04101 | 2/1997 |
| WO | WO 03/016508 | 2/2003 |
| WO | WO 03/089634 | 10/2003 |
| WO | WO 03/104445 | 12/2003 |
| WO | WO 2004/029235 | 4/2004 |
| WO | WO 2004/029269 | 4/2004 |

OTHER PUBLICATIONS

Wells, Biochemistry, vol. 29, pp. 8509-8517, 1990.*
Seffernick et al. (J. Bacteriology, vol. 183, pp. 2405-2410, 2001).*
Saito et al., "Cloning Of Genes Coding For L-Sorbose And L-Sorbosone Dehydrogenases From *Gluconobacter oxydans* And Microbial Production Of 2-Keto-L-Gulonate, A Precursor Of L-Ascorbic Acid, In A Recombinant *G. oxydans* Strain," App. & Environ. Microbiol., vol. 63, No. 2, pp. 454-460 (1997).
Database EMBL [Online], "*Agrobacterium tumefaciens Str. C58* Linear Chromosome, Section 35 of 187 Of The Complete Sequence," XP002321379, EBI accession No. EM_PRO:AE009265 (2001).
Database Uniprot [Online], "Glucose Dehydrogenase," XP002321380, EBI accession No. UNIPROT:Q882Q7 (2003).
Sugisawa et al., "Isolation And Characterization Of A New Vitamin C Producing Enzyme (L-Gulono-γ-lactone Dehydrogenase) Of Bacterial Origin," Biosci., Biotech., & Biochem., XX, XX, vol. 59, No. 2, pp. 190-196 (1995).
Sugisawa et al., "Microbial Production Of 2-Keto-L-Gulonic Acid From L-Sorbose And D-Sorbitol by *Gluconobacter melanogenus*," Agr. & Biol. Chem., vol. 54, No. 5, pp. 1201-1209 (1990).
Lee et al., "Screening For L-Sorbose And L-Sorbosone Dehydrogenase Producing Microbes For 2-Keto-L-Gulonic Acid Production," J. of Indus. Microbiol. & Biotech., vol. 23, No. 2, pp. 106-111 (1999).
Shinjoh et al., "Cloning And Nucleotide Sequencing Of The Membrane-Bound L-Sorbosone Dehydrogenase Gene Of *Acetobacter liquefaciens* IFO 12258, and Its Expression In *Gluconobacter oxydans*," Appl. & Environ. Microbiol., vol. 61, No. 2, pp. 413-420 (1995).

* cited by examiner

*Primary Examiner*—Hope A Robinson
(74) *Attorney, Agent, or Firm*—Hoxie & Associates LLC

(57) ABSTRACT

The present invention discloses an isolated polynucleotide molecule derived from a polynucleotide encoding a polypeptide having L-sorbosone dehydrogenase activity comprising a partial nucleotide sequence of at least 20 consecutive nucleotides of SEQ ID NO:1. The present invention further relates to a process for the production of L-ascorbic acid in high yield, in particular a process using resting cells of a microorganism able to convert given carbon sources into vitamin C. The thus obtained vitamin C may be further processed by purification and/or separation steps.

4 Claims, No Drawings

POLYPEPTIDES AND ENCODING POLYNUCLEOTIDES FOR MICROBIAL PRODUCTION OF L-ASCORBIC ACID AND ASSOCIATED METHODS

This application is a U.S. filing under 35 U.S.C. 271 of PCT/CH2004/00511, filed Aug. 16, 2004, which claims the benefit of EP 030176677.0, filed on Aug. 14, 2003, the contents of each of which are herein incorporated by reference. The present invention relates to polynucleotides derived from polynucleotides which encode an enzyme which converts L-sorbosone directly to L-ascorbic acid. The enzyme L-sorbosone dehydrogenase (in the following: SNDHai) produces L-ascorbic acid (vitamin C) directly from L-sorbosone. The L-sorbosone dehydrogenase (SNDHai) was derived from bacteria belonging to the genera *Gluconobacter* and *Acetobacter*. The present invention further relates to a process for the production of L-ascorbic acid in high yield. L-Ascorbic acid is widely used in the pharmaceutical, food and cosmetic industries.

For the past 70 years, L-ascorbic acid (vitamin C) has been produced industrially from D-glucose by the well-known Reichstein method. All steps in this process are chemical except for one (the conversion of D-sorbitol to L-sorbose) which is carried out by microbial transformation. Since its initial implementation for industrial production of L-ascorbic acid, several chemical and technical modifications have been used to improve the efficiency of the Reichstein method. Recent developments of vitamin C production are summarized in Ullmann's Encyclopedia of Industrial Chemistry, $5^{th}$ Edition, Vol. A27 (1996), pp. 547ff. Recently different steps of vitamin C production have been performed with the help of microorganisms or enzymes isolated therefrom.

Current production methods for L-ascorbic acid have some undesirable characteristics such as high-energy consumption and use of large quantities of organic and inorganic solvents. Therefore, over the past decades, other approaches to manufacture L-ascorbic acid using microbial conversions, which would be more economical as well as ecological, have been investigated. Direct L-ascorbic acid production has been reported in several microorganisms.

Surprisingly, it has now been found that the direct conversion of L-sorbosone to L-ascorbic acid can be performed using the L-sorbosone dehydrogenase (hereafter called SNDHai) isolated from *G. oxydans* N44-1 or enzymes which are orthologs thereof originating from acetic acid bacteria belonging to the genera *Gluconobacter* and *Acetobacter*. A gene responsible for this reaction was isolated and the sequence was determined. The sorbosone dehydrogenase enzyme encoded by this gene converts L-sorbosone to L-ascorbic acid. This enzyme is different from the known SNDH enzymes.

L-ascorbic acid or vitamin C as used interchangeably herein may be any chemical form of L-ascorbic acid found in aqueous solutions, such as for instance undissociated, in its free acid form or dissociated as an anion. The solubilized salt form of L-ascorbic acid may be characterized as the anion in the presence of any kind of cations usually found in fermentation supernatants, such as for instance potassium, sodium, ammonium, or calcium. Also included may be isolated crystals of the free acid form of L-ascorbic acid. On the other hand, isolated crystals of a salt form of L-ascorbic acid are called by their corresponding salt name, i.e. sodium ascorbate, potassium ascorbate, calcium ascorbate and the like.

Conversion of L-sorbosone into vitamin C means that the conversion of the substrate resulting in vitamin C is performed by SNDHai, i.e. the substrate may be directly converted into vitamin C.

A cloning vector may be for instance any plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication. The cloning vector may further contain for instance a marker suitable for use in the identification of cells transformed with the cloning vector. Such markers may provide for instance resistance to antibiotics, such as for instance tetracycline or ampicillin.

An expression vector may be any vector which is capable of enhancing the expression of a gene that has been cloned into it, after for instance transformation into a host. The cloned gene is usually placed under the control of (i.e., operably linked to) certain control sequences such as for instance promoter sequences. Promoter sequences may be either constitutive or inducible.

A nucleic acid molecule may include DNA and RNA. Any form, such as for instance double-stranded, single-stranded nucleic acid, and nucleosides thereof may be useful as nucleic acid molecule. Also included are hybrids such as for instance DNA-RNA hybrids, DNA-RNA-protein hybrids, RNA-protein hybrids, and DNA-protein hybrids. A polynucleotide may consist of several bases, usually at least 20 nucleotide bases.

The term "homology" designates the similarity of two polynucleotide sequences. In order to determine the homology the polynucleotide sequences are arranged in such a manner, that similar areas can be compared. If required, nucleotides at certain positions may be replaced by a blank position in order to improve the similarity. Homology comparisons may be performed for instance by hand or by using computer programs which are commercially available. Preferably the program is run under standard conditions in order to obtain the maximum homology. The degree of homology or similarity between two nucleotide sequences is given in "% homology".

A mutation may be for instance a single base pair change, insertion or deletion in the nucleotide sequence of interest or a genetic event such as an insertion of a genetic element like for instance a transposon.

The generation of a mutation into the DNA, i.e. mutagenesis, may be performed in different ways, such as for instance randomly, i.e. random mutagenesis, wherein the exact site of mutation is not predictable, occurring anywhere in the chromosome(s) of the microorganism or on the endogenous plasmid(s). The mutation may be also generated as for instance a result of physical damage caused by agents such as for instance radiation, chemical treatment, or insertion of a genetic element.

As promoter may be used any DNA sequence which is located proximal to the start codon of a respective gene and which initiates the transcription of one or more adjacent gene(s). In general, the promoter may be located at the 5' region of a respective gene. The promoter may be an inducible or constitutive promoter. In the case of an inducible promoter, the rate of transcription increases in response to an inducing agent. In case of a constitutive promoter, the rate of transcription is not regulated by for instance an inducing agent.

The term "identity" and "% identity" refers to the comparison of two amino acid sequences using a sequence analysis program as for instance exemplified below. "% identical" refers to the percent of the amino acids of the subject amino acid sequence that have been matched to identical amino acids in the compared amino acid sequence. If both amino acid sequences which are compared do not differ in any of their amino acids, they are identical or have 100% identity.

In one embodiment the present invention is related to an isolated polynucleotide derivable from a polynucleotide molecule encoding a polypeptide having L-sorbosone dehydrogenase activity comprising a partial nucleotide sequence of SEQ ID NO:1 of at least 20 consecutive nucleotides. Thus, the present invention provides an isolated polynucleotide molecule derived from a polynucleotide encoding a polypeptide having L-sorbosone dehydrogenase activity comprising a partial nucleotide sequence of at least 20 consecutive nucleotides of SEQ ID NO:1. The isolated polynucleotide comprises preferably a partial nucleotide sequence of at least 50 and more preferably of at least 100 consecutive nucleotides of SEQ ID NO:1. Most preferred is an isolated polynucleotide comprising the nucleotide sequence of SEQ ID NO:1. Further most preferred embodiment is an isolated polynucleotide comprising a nucleotide sequence selected from the group consisting of SEQ ID NOs:11, 13, 15, 17, 19, 21 and 26. The isolated polynucleotide may be derived from a polynucleotide which codes for a polypeptide having L-sorbosone dehydrogenase activity. SEQ ID NO:1 represents the complete nucleotide sequence of SNDHai which was isolated from the microorganism Gluconobacter oxydans N44-1. Parts of such a sequence may be used for different purposes. Short polynucleotides for example may be used as primers for, e.g., the amplification of suitable polynucleotides isolated from other organisms. A short polynucleotide can be in the range of about 10 to about 100 base pairs (bp), usually about 14 to about 50, and preferably about 17 to about 30 bp. Examples of such short polynucleotide sequences are represented by SEQ ID NOs:5, 6, 7, 8, 9, 10, 23 or 24. Longer polynucleotides may code for polypeptides having enzymatic activity. For example, the SNDHai has a transmembrane domain which may not be used for enzymatic activity. If parts of the polynucleotide coding for the enzymatically active area of the protein are expressed without the transmembrane domain, such a polypeptide may have sufficient enzymatic activity.

The isolated polynucleotide molecule is usually derived from a longer polynucleotide sequence which codes also for a polypeptide having L-sorbosone dehydrogenase activity. Such polynucleotides may be isolated for instance from bacteria. Preferably they are isolated from bacteria belonging to the genera Gluconobacter and Acetobacter including, but not limited to, G. oxydans, G. frateurii, G. cerinus and A. aceti. When such polynucleotides are derived from longer polynucleotide sequences it is possible to determine the homology between such a polynucleotide sequence and SEQ ID NO:1. In such a case preferably an area having at least 100 consecutive nucleotides is selected and the corresponding stretch from the other polynucleotide can be compared therewith. When the polynucleotide sequence and the corresponding stretch derivable from SEQ ID NO:1 have for instance 60 nucleotides which are identical by comparing 100 consecutive nucleotides then the homology is 60%. Thus, in one embodiment the invention is directed to an isolated polynucleotide according to the present invention wherein the partial nucleotide sequence is derived from a polynucleotide sequence having a homology of at least 60% with SEQ ID NO:1 whereby at least 100 consecutive nucleotides are compared. Preferably, the partial polynucleotide sequences of the present invention have a homology of at least 80% and more preferably of at least 90% with SEQ ID NO:1. For the determination of the homology stretches of for instance at least 100 may be used, preferably stretches of at least 300 and more preferably stretches of at least 500 consecutive nucleotides.

The present invention provides novel polynucleotide sequences coding for L-sorbosone dehydrogenase of a microorganism belonging to acetic acid bacteria including the genera Gluconobacter and Acetobacter for producing L-ascorbic acid from L-sorbosone. The said polynucleotide preferably codes for a polypeptide having the amino acid sequence of SEQ ID NO:2 or a polypeptide derived or derivable from said polypeptide by for instance substitution, deletion, insertion or addition of one or more amino acids in the amino acid sequence of SEQ ID NO:2, which retains L-sorbosone dehydrogenase activity to produce L-ascorbic acid from L-sorbosone. Further included are polynucleotide sequences coding for partial polypeptide sequences of a polypeptide which retains L-sorbosone dehydrogenase activity to produce L-ascorbic acid from L-sorbosone such as, for example, polypeptides represented by SEQ ID NOs:12, 14, 16, 18, 20, 22, and 27.

The polypeptides of the present invention comprise preferably partial amino acid sequences of at least 25 consecutive amino acids selected from the amino acids sequences of the polypeptides disclosed in the present application. The person skilled in the art is aware of the fact that certain stretches in polypeptides are essential for the biological activity. There are, however, other areas wherein amino acids can be inserted, deleted or substituted by other amino acids preferably such amino acids which are similar to the amino acids to be replaced.

This invention is further directed to recombinant DNA molecules and/or expression vectors comprising a polynucleotide of the present invention, especially one which functions in a suitable host cell.

Any cell that serves as recipient of foreign nucleotide acid molecule(s) may be used as a host cell, such as for instance a cell carrying a replicable expression vector or cloning vector or a cell being genetically engineered by well known techniques to contain desired gene(s) on its chromosome(s) or genome. The host cell may be of prokaryotic or eukaryotic origin, such as, for instance bacterial cells, animal cells, including human cells, fungal cells, including yeast cells, and plant cells. Preferably the host cell belongs to bacteria that can express the L-sorbosone dehydrogenase as an active form in vivo, more preferably bacteria of the genera Gluconobacter, Acetobacter, Pseudomonas, such as P. putida, or Escherichia, such as E. coli.

Thus, it is an aspect of the present invention to provide a host cell as described above, comprising such an expression vector or comprising such a nucleotide which has the polynucleotide integrated in its chromosomal DNA. Such host cell is then called a recombinant host cell or recombinant organism.

This invention is further directed to a process for producing a recombinant L-sorbosone dehydrogenase polypeptide encoded by a polynucleotide of this invention. Such process includes for instance the cultivation of any of the recombinant organisms of this invention as described specifically above. Accordingly, part of this invention is the recombinant L-sorbosone dehydrogenase polypeptide produced by this process. Such recombinant L-sorbosone dehydrogenase may be used for instance as a soluble enzyme in any standard procedure used for enzymatic reactions and known to a skilled person, recycled by use of devices such as membrane modules or membrane reactors, or immobilized on a solid carrier for solid phase enzymatic reaction.

Another aspect of this invention is a process for producing L-ascorbic acid comprising converting a substrate into L-ascorbic acid with the aid of the recombinant L-sorbosone dehydrogenase polypeptide encoded by a polynucleotide of this invention. The use of an L-sorbosone dehydrogenase (SNDHai) isolated from a microorganism producing such enzyme naturally, i.e., non-recombinantly, wherein the isolated SNDHai is encoded by a polynucleotide of this invention, is also included by the present invention.

As substrate may be used a carbon source that can be converted into L-ascorbic acid by the SNDHai as encoded by a polynucleotide of the present invention. Preferred substrates are selected from L-sorbose, D-sorbitol, and L-sorbosone.

In one embodiment of this invention, the process for producing L-ascorbic acid comprises converting L-sorbose or D-sorbitol into L-ascorbic acid in a host cell having the ability for converting L-sorbose into L-sorbosone or for converting D-sorbitol into L-sorbosone.

In another embodiment, the process for the production of L-ascorbic acid comprises converting L-sorbosone into L-ascorbic acid with the aid of the recombinant SNDHai encoded by a polynucleotide of this invention. L-sorbosone dehydrogenase (SNDHai) isolated from a microorganism producing such enzyme naturally, i.e., non-recombinantly, wherein the isolated SNDHai is encoded by a polynucleotide of this invention, may be also used for such a process.

The invention provides isolated nucleic acid molecules encoding the enzyme (L-sorbosone dehydrogenase SNDHai or parts thereof). Methods and techniques designed for the manipulation of isolated nucleic acid molecules are well known in the art. Methods for the isolation, purification, and cloning of nucleic acid molecules, as well as methods and techniques describing the use of eukaryotic and prokaryotic hosts and nucleic acid and protein expression therein, are known to the skilled person.

Functional derivatives of polypeptides of the present invention may be also part of the present invention and are defined on the basis of the amino acid sequences of the present invention by addition, insertion, deletion and/or substitution of one or more amino acid residues of such sequences wherein such derivatives preferably still have the L-sorbosone dehydrogenase activity measured by an assay known in the art or specifically described herein. Such functional derivatives may be made either by chemical peptide synthesis known in the art or by recombinant techniques on the basis of the DNA sequences as disclosed herein by methods known in the state of the art. Amino acid exchanges in proteins and peptides which do not generally alter the activity of such molecules are known.

In particular embodiments of the present invention, conservative substitutions of interest occur as follows: as example substitutions, Ala to Val/Leu/Ile, Arg to Lys/Gln/Asn, Asn to Gln/His/Lys/Arg, Asp to Glu, Cys to Ser, Gln to Asn, Glu to Asp, Gly to Pro/Ala, His to Asn/Gln/Lys/Arg, Ile to Leu/Val/Met/Ala/Phe/norLeu, Lys to Arg/Gln/Asn, Met to Leu/Phe/Ile, Phe to Leu/Val/Ile/Ala/Tyr, Pro to Ala, Ser to Thr, Thr to Ser, Trp to Tyr/Phe, Tyr to Trp/Phe/Thr/Ser, and Val to Ile/Leu/Met/Phe/Ala/norLeu are reasonable. As preferred examples, Ala to Val, Arg to Lys, Asn to Gln, Asp to Glu, Cys to Ser, Gln to Asn, Glu t Asp, Gly to Ala, His to Arg, Ile to Leu, Leu to Ile, Lys to Arg, Met to Leu, Phe to Leu, Pro to Ala, Ser to Thr, Thr to Ser, Trp to Tyr, Tyr to Phe, and Val to Leu are reasonable. If such substitutions result in a change in biological activity, then more substantial changes, denominated exemplary substitutions described above, are introduced and the products screened.

Unless otherwise indicated, all nucleotide sequences determined by sequencing a DNA molecule herein were determined using an automated DNA sequencer (such as the model Applied Biosystems PRISM 310 genetic analyzer). Therefore, as is known in the art for any DNA sequence determined by this automated approach, any nucleotide sequence determined herein may contain some errors. Nucleotide sequences determined by automation are typically at least about 90% homologous, more typically at least about 95% to at least about 99.9% homologous to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

In a preferred embodiment the present invention is directed to polynucleotides encoding polypeptide having the L-sorbosone dehydrogenase activity as disclosed in the sequence listing as SEQ ID NO:2 as well as the complementary strands, or those which include these sequences, DNA sequences or fragments thereof, and DNA sequences, which hybridize under standard conditions with such sequences but which encode for polypeptides having exactly the same amino acid sequence.

Another mode of describing the similarity of polynucleotide sequences is to determine whether such sequences do hybridize or do not hybridize. This depends on the conditions selected for the hybridization.

Standard conditions for hybridization mean in this context such conditions which are generally used by a person skilled in the art to detect specific hybridization signals, or preferably so called "stringent hybridization conditions" used by a person skilled in the art. Thus, as used herein, the term "stringent hybridization conditions" means that hybridization will occur if there is about 95% and preferably at least 97% homology between the sequences. Stringent hybridization conditions are, e.g., 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

In one aspect, the gene encoding L-sorbosone dehydrogenase, the nucleic acid molecule containing said gene, the expression vector and the recombinant organism used in the present invention may be obtained by the following steps:

(1) transposon mutagenesis as described below on the strains belonging to the genus *Gluconobacter* or *Acetobacter* strains that produces L-ascorbic acid from L-sorbosone to obtain colonies expressing antibiotic resistance encoded by the transposon used;

(2) selection of L-ascorbic acid non-producing mutants in the screening with L-sorbosone as a substrate;

(3) isolation of chromosomal DNA from the mutants;

(4) cloning of the DNA fragment containing the transposon from the chromosomal DNA by colony-, plaque-, or Southern-hybridization, PCR (polymerase chain reaction) cloning, and so on;

(5) determination of the nucleotide sequence of the DNA fragment containing the transposon insertion;

(6) cloning of the DNA fragment from the parent strain that produces L-ascorbic acid from L-sorbosone;

(7) construction of the expression vector on which the gene coding for L-sorbosone dehydrogenase can express efficiently;

(8) construction of recombinant organisms carrying the gene coding for L-sorbosone dehydrogenase by an appropriate method for introducing DNA into host cell, e.g. transformation, transduction, conjugal transfer and/or electroporation, which host cell thereby becomes a recombinant organism of this invention.

Transposon mutagenesis is known as a potent tool for genetic analysis (P. Gerhardt et al., "Methods for General and Molecular Bacteriology" Chapter 17, Transposon Mutagenesis; American Society for Microbiology).

A variety of transposons is known in the art, such as Tn3, Tn5, Tn7, Tn9, Tn10, phage Mu and the like. Among them, Tn5 is known to have almost no insertion specificity, and its size is relatively small. For the purpose of use in the random mutagenesis in the practice of the present invention, Tn5 is preferred. A variety of Tn5 derivatives, designated Mini-Tn5s, which consist of 19 bp of the Tn5 inverted repeats required for transposition coupled to antibiotic resistance or other selectable marker genes are also useful for the present invention. Such Mini-Tn5s are inserted into a suicide vector, in addition to the Tn5 transposase (tnp), to construct an efficient suicide Tn5 mutagenesis system.

Random mutagenesis with transposon involves the introduction of a transposon into a target bacterial cell via for instance transformation, transduction, conjugal mating or electroporation by using suicide plasmid or phage vectors. The resulting mutants may be screened with the aid of the marker carried by the transposon. Transposition of the transposon into the genome of the recipient bacterium may be detected after the vector used has been lost by segregation.

For the introduction of transposons into a microorganisms of the genus *Gluconobacter* or *Acetobacter*, so-called suicide vectors including for instance a derivative of phage P1 and narrow-host-range plasmids such as a derivative of pBR325 carrying ColE1 replication origin are commonly used. The phage P1 vectors and the plasmid vectors may be transferred by infection and by transformation, conjugal mating or electroporation, respectively, into the recipient cells, wherein these vectors preferably lack the appropriate origins of recipients. The choice of suicide vector and transposon to be used depends on criteria including for instance phage sensitivity, intrinsic antibiotic resistance of the recipient cell, the availability of a gene transfer system including transformation, conjugal transfer, electroporation, or infection to introduce transposon-carrying vector into *E. coli*.

One of the preferable vectors for use in the present invention is for instance phage P1 (ATCC25404) which injects its DNA into a microorganism belonging to the genus *Gluconobacter* or *Acetobacter*, however, this DNA will be unable to replicate and will be lost by segregation. Such P1 phage carrying Tn5 (P1::Tn5) may be used in the form of phage lysates which may be prepared by lysing *E. coli* carrying P1::Tn5 in accordance with known procedures (see: e.g. "Methods for General and Molecular Bacteriology" Chapter 17, Transposon Mutagenesis; American Society for Microbiology or U.S. Pat. No. 5,082,785, 1992).

For confirming that the deficient mutant really carries the transposon, methods such as for instance colony- or Southern-hybridization may be conducted with labeled-DNA fragments containing the transposon used as the probe by standard methods (Molecular cloning, a laboratory manual second edition, Maniatis T., et al., 1989).

Such a mutant was isolated as described in Example 5 of the present invention. The transposon mutant may be useful for further identifying the target gene coding for L-sorbosone dehydrogenase and determining the nucleotide sequence of the region tagged with the transposon.

The DNA fragment containing a transposon insertion may be cloned into any *E. coli* cloning vectors, preferably pUC18, pUC19, pBluescript II KS+ (Stratagene Europe) and their relatives, by selecting transformants showing both phenotypes of selection markers of the vector and the transposon. The nucleotide sequences adjacent to the transposon may be determined by sequencing methods known in the art.

Alternatively, when the said L-sorbosone dehydrogenase polypeptide is purified from the strain producing L-ascorbic acid from L-sorbosone, the desired gene may be cloned in either plasmid or phage vectors from a total chromosomal DNA by the following illustrative methods:

(i) The partial amino acid sequences can be determined from the purified proteins or peptide fragments thereof by methods such as, for instance, matrix assisted laser desorption/ionization (MALDI). Such whole protein or peptide fragments may be prepared by the isolation of such a whole protein or by peptidase-treatment from the gel after SDS-polyacrylamide gel electrophoresis (SDS-PAGE). Thus obtained protein or fragments thereof may also be applied to a protein sequencer such as Applied Biosystems automatic gas-phase sequencer 470A. The amino acid sequences may be utilized to design and prepare oligonucleotide probes and/or primers with DNA synthesizer such as for instance Applied Biosystems automatic DNA sequencer 381A. The probes may be used for isolating clones carrying the target gene from a gene library of the strain carrying the target gene by means of for instance Southern-, colony- or plaque-hybridization.

(ii) Further alternatively, for the purpose of selecting clones expressing the target protein from the gene library, immunological methods with for instance an antibody prepared against the target protein may be applied.

(iii) The DNA fragment of the target gene may be amplified from the total chromosomal DNA by for instance PCR with a set of primers, i.e. two oligonucleotides synthesized according to the amino acid sequences determined as above. Then a clone carrying the whole gene may be isolated from the gene library constructed, e.g. in *E. coli* by for instance Southern-, colony-, or plaque-hybridization with the PCR product obtained above as the probe.

DNA sequences which may be made by PCR using primers designed on the basis of the DNA sequences disclosed therein by methods known in the art are also an object of the present invention.

The above-mentioned antibody may be prepared for instance with the purified L-sorbosone dehydrogenase proteins, the purified recombinant L-sorbosone dehydrogenase proteins such as for instance His-tagged L-sorbosone dehydrogenase expressed in *E. coli*, or its peptide fragment as an antigen. A polypeptide sequence deduced from a nucleotide sequence of the L-sorbosone dehydrogenase may be used as an antigen for preparation of an antibody.

Once a clone carrying the desired gene is obtained, the nucleotide sequence of the target gene may be determined by a well-known method.

To express the desired gene/nucleotide sequence efficiently, various promoters may be used; e.g., the original promoter of the gene, promoters of antibiotic resistance genes such as for instance kanamycin resistant gene of Tn5, ampicillin resistant gene of pBR322, and beta-galactosidase of *E. coli* (lac), trp-, tac-, trc-promoter, promoters of lambda phage and any promoters which may be functional in the host cell. For this purpose, the host cell may be selected from a group consisting of bacterial cells, animal cells, including human cells, fungal cells, including yeast cells, and plant cells. Preferably the host cell belongs to bacteria that can express the L-sorbosone dehydrogenase as an active form in vivo, in particular bacteria of the genera *Gluconobacter, Acetobacter, Pseudomonas* and *Escherichia*.

For expression, other regulatory elements, such as for instance a Shine-Dalgarno (SD) sequence (e.g., AGGAGG and so on including natural and synthetic sequences operable in the host cell) and a transcriptional terminator (inverted repeat structure including any natural and synthetic sequence) which are operable in the host cell (into which the coding sequence will be introduced to provide a recombinant cell of this invention) may be used with the above described promoters.

A wide variety of host/cloning vector combinations may be employed in cloning the double stranded DNA. Preferred vectors for the expression of the gene of the present invention, i.e. the SNDHai gene, in *E. coli* may be selected from any vectors usually used in *E. coli*, such as for instance pQE vectors which can express His-tagged recombinant proteins (QIAGEN AG Switzerland), pBR322 or its derivatives including for instance pUC18 and pBluescript II (Stratagene Cloning Systems, Calif., USA), pACYC177 and pACYC184 and their derivatives, and a vector derived from a broad host range plasmid such as RK2 and RSF1010. A preferred vector for the expression of the nucleotide sequence of the present invention in bacteria including *Gluconobacter, Acetobacter*, and *Pseudomonas* is selected from any vectors which can replicate in *Gluconobacter, Acetobacter*, or *Pseudomonas* as well as in a preferred cloning organism such as *E. coli*. The preferred vector is a broad-host-range vector such as for instance a cosmid vector like pVK100 and its derivatives and RSF1010. Copy number and stability of the vector should be carefully considered for stable and efficient expression of the cloned gene and also for efficient cultivation of the host cell carrying the cloned gene. Nucleic acid molecules containing for instance transposable elements such as Tn5 may also be used as a vector to introduce the desired gene into the preferred host, especially on a chromosome. Nucleic acid molecules containing any DNAs isolated from the preferred host together with the SNDHai gene of the present invention may be also useful to introduce this gene into the preferred host cell, especially on a chromosome. Such nucleic acid molecules may be transferred to the preferred host by applying any of a conventional methods, e.g., transformation, transduction, conjugal mating or electroporation, which are well known in the art, considering the nature of the host cell and the nucleic acid molecule.

The L-sorbosone dehydrogenase gene/nucleotide sequences provided in this invention may be ligated into a suitable vector containing a regulatory region such as for instance a promoter, a ribosomal binding site, and a transcriptional terminator operable in the host cell described above with a well-known method in the art to produce an expression vector.

To construct a recombinant microorganism carrying an expression vector, various gene transfer methods including for instance transformation, transduction, conjugal mating, and electroporation may be used. The method for constructing a recombinant cell may be selected from the methods well-known in the field of molecular biology. For instance, conventional transformation systems may be used for *Gluconobacter, Acetobacter, Pseudomonas*, or *Escherichia*. A transduction system may also be used for *E. coli*. Conjugal mating system may be widely used in Gram-positive and Gram-negative bacteria including for instance *E. coli, P. putida*, and *Gluconobacter*. An example of conjugal mating is disclosed in WO 89/06,688. The conjugation may occur in for instance liquid medium or on a solid surface. Examples for a recipient for SNDHai production include for instance microorganisms of *Gluconobacter, Acetobacter, Pseudomonas*, or *Escherichia*. To the recipient for conjugal mating, a selective marker may be added; e.g., resistance against nalidixic acid or rifampicin is usually selected. Natural resistance may also be used, e.g., resistance against polymyxin B is useful for many *Gluconobacters*.

The present invention provides recombinant L-sorbosone dehydrogenase (SNDHai). One may increase the production yield of the L-sorbosone dehydrogenase enzyme by introducing the L-sorbosone dehydrogenase gene provided by the present invention into host cells described above. In one aspect, the L-sorbosone dehydrogenase proteins are produced in a host cell selected from a group consisting of *Gluconobacter, Acetobacter, Pseudomonas*, or *Escherichia* by using the L-sorbosone dehydrogenase gene of the present invention.

The microorganism which is able to express SNDHai as encoded by a polynucleotide sequence of the present invention may be cultured in an aqueous medium supplemented with appropriate nutrients under aerobic conditions. The cultivation may be conducted in batch, fed-batch, semi-continuous or continuous mode. The cultivation period may vary depending on for instance the host used for expression of the target polypeptide, pH, temperature and nutrient medium to be used, and is preferably about 1 to about 10 days when run in batch or fed-batch mode. The cultivation may be conducted at for instance a pH of about 4.0 to about 9.0, preferably about 5.0 to about 8.0. The preferred temperature range for carrying out the cultivation is from about 13° C. to about 36° C., preferably from about 18° C. to about 33° C. Usually, the culture medium may contain such nutrients as assimilable carbon sources, e.g., glycerol, D-mannitol, D-sorbitol, L-sorbose, erythritol, ribitol, xylitol, arabitol, inositol, dulcitol, D-ribose, D-fructose, D-glucose, and sucrose, preferably D-sorbitol, D-mannitol, and glycerol; and digestible nitrogen sources such as organic substances, e.g., peptone, yeast extract, baker's yeast, urea, amino acids, and corn steep liquor. Various inorganic substances may also be used as nitrogen sources, e.g., nitrates and ammonium salts. Furthermore, the culture medium usually may contain inorganic salts, e.g., magnesium sulfate, manganese sulfate, potassium phosphate, and calcium carbonate.

It is understood that the process for the production of vitamin C from the substrate using a host comprising the SNDHai encoded by a polynucleotide as of the present invention is performed with growing cells, i.e., specific growth rates of the cells which are for instance at least 0.02 $h^{-1}$.

One embodiment of the present invention is the use of isolated SNDHai encoded by a nucleotide sequence as disclosed herein for the production of vitamin C. For isolation and purification of SNDHai from the microorganism after cultivation, the cells of the microorganism may be harvested from the liquid culture broth by for instance centrifugation or filtration. The harvested cells may be washed for instance with water, physiological saline or a buffer solution having an appropriate pH. The washed cells may be suspended in an appropriate buffer solution and disrupted by means of for instance a homogenizer, sonicator, French press, or by treatment with lysozyme and the like to give a solution of disrupted cells. The L-sorbosone dehydrogenase may be isolated and purified from the cell-free extract or disrupted cells, preferably from the membrane fraction by standard methods such as for instance ultracentrifugation, differential solubilization using appropriate detergents, precipitation by salts or other suitable agents, dialysis, ion exchange chromatographies, hydroxyapatite chromatographies, hydrophobic chromatographies, size exclusion chromatographies, affinity chromatographies, or crystallization. When the recombinant L-sorbosone dehydrogenase is produced as tagged polypeptide such as for instance a His-tag one, it may be purified with affinity resins such as for instance Nickel affinity resin. The purification of L-sorbosone dehydrogenase may be monitored photometrically by using for instance artificial electron acceptors such as nitrobluetetrazolium chloride (NBT) and phenazine methosulfate, 2,6-dichlorophenol indophenole (DCIP), ferricyanide or cytochrome c.

The production of L-ascorbic acid with the help of the SNDHai as described herein is provided by the present invention. The source for the SNDHai is not critical. This process may be performed by using for instance microorganisms able to naturally express active SNDHai enzyme, SNDHai encoded by a nucleotide sequence of the present invention which is isolated from said microorganisms, recombinant organisms as described above carrying the SNDHai gene of the present invention, or by using the native and/or recombinant SNDHai in the form of a membrane fraction, soluble or immobilized enzyme acting as a biocatalyst to convert L-sorbosone into L-ascorbic acid as described below. The above described method for the isolation and purification of SNDHai may be used for both the native and recombinant SNDHai.

Recombinant organisms used for the production of L-ascorbic acid from L-sorbosone may be cultivated as described above. Preferably, the recombinant organism is selected from the group consisting of *Gluconobacter, Acetobacter, Pseudomonas*, and *Escherichia* carrying the L-sorbosone dehydrogenase gene of the present invention. The recombinant microorganism may be cultured under the same conditions as described above. If the recombinant organism being used for production of L-ascorbic acid is not able to convert any of the carbon sources described above into L-sorbosone, then L-sorbosone has to be added to the medium to be used as the precursor for the production of L-ascorbic acid. The reaction period may vary depending on the pH, temperature and reaction mixture to be used, and is preferably about 1 to about 10 days when run in batch or fed-batch mode.

In one embodiment, the SNDHai of the present invention, either as recombinant or native, i.e. isolated non-recombinant enzyme, is purified from the culture medium as described above and used in the form of soluble or immobilized enzyme as a biocatalyst to convert L-sorbosone into L-ascorbic acid in any process mode known to the skilled person, such as batch, fed-batch, semi-continuous or continuous mode. The purified L-sorbosone dehydrogenase may be used for instance as such in soluble form, retained in the reaction vessel by means of membrane devices, or as immobilized enzyme in any solid phase such as for instance porous or polymeric matrixes. For instance, the enzyme may be bound directly to a membrane, granules or the like of a resin having one or more functional groups, or it may be bound to the resin through bridging compounds having one or more functional groups, for example, glutaraldehyde. The reaction using purified enzyme in soluble, retained or immobilized form may take place for instance in aqueous medium containing L-sorbosone and other appropriate nutrients under aerobic conditions. The reaction medium may contain for instance inorganic salts, e.g., magnesium sulfate, potassium phosphate, and calcium carbonate. The reaction may be conducted at a pH of about 4.0 to about 9.0, preferably about 5.0 to about 8.0. The preferred temperature range for carrying out the reaction is from about 13° C. to about 36° C., preferably from about 18° C. to about 33° C.

Microorganisms which can be used for the present invention may be publicly available from different sources, e.g., Deutsche Sammlung von Mikroorganismen und Zellkulturen (DSMZ), Mascheroder Weg 1B, D-38124 Braunschweig, Germany, American Type Culture Collection (ATCC), P.O. Box 1549, Manassas, Va. 20108 USA on May 12, 2003 or Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Juso-honmachi 2-chome, Yodogawa-ku, Osaka 532-8686, Japan). Examples of preferred bacteria deposited with IFO are for instance *Gluconobacter oxydans* (formerly known as *G. melanogenus*) IFO 3293, *Gluconobacter oxydans* (formerly known as *G. melanogenus*) IFO 3292, *Gluconobacter oxydans* (formerly known as *G. rubiginosus*) IFO 3244, *Gluconobacter frateurii* (formerly known as *G. industrius*) IFO 3260, *Gluconobacter cerinus* IFO 3266, *Gluconobacter oxydans* IFO 3287, and *Acetobacter aceti* subsp. *orleanus* IFO 3259, which were all deposited on Apr. 5, 1954; *Acetobacter aceti* subsp. *xylinum* IFO 13693 deposited on Oct. 22, 1975, and *Acetobacter aceti* subsp. *xylinum* IFO 13773 deposited on Dec. 8, 1977. Strain *Acetobacter* sp. ATCC 15164, which is also an example of a preferred bacterium, was deposited with ATCC. Strain *Gluconobacter oxydans* (formerly known as *G. melanogenus*) N44-1 as another example of a preferred bacterium is a derivative of the strain IFO 3293 and is described in Sugisawa et al., Agric. Biol. Chem. 54: 1201-1209, 1990.

It is understood that the above-mentioned microorganisms also include synonyms or basonyms of such species having the same physiological properties, as defined by the International Code of Nomenclature of Prokaryotes.

In a further aspect, the present invention relates to a novel process for the production of L-ascorbic acid (vitamin C) in high yield by using resting cells of a microorganism able to convert given carbon sources into vitamin C.

Direct L-ascorbic acid production has been reported in several microorganisms, using different cultivation methods. The disadvantage of such processes, however, is the low yield of vitamin C produced due to the instability of the product. Using, for instance, microorganisms which are known to be both capable of the production of 2-keto-L-gulonic acid (2-KGA) and vitamin C, the yield of microbiologically produced vitamin C is further limited by the relatively high production of 2-KGA which is more readily synthesized by said microorganism, leading, for instance, to ratios between the concentration of vitamin C and 2-KGA which are less than 0.1. Thus, it is an object of the present invention to improve the microbiological production of vitamin C to get higher yields as with the processes described in the prior art.

Surprisingly, it has now been found that a process using resting cells of a microorganism capable of performing the direct conversion of a substrate to vitamin C leads to higher yields of vitamin C.

In particular, the present invention provides a process for the production of vitamin C comprising converting a substrate into vitamin C in a medium comprising resting cells of a microorganism.

As substrate for the above process using resting cells of a microorganism may be used a carbon source that can be converted into L-ascorbic acid and which is easily obtainable from the D-glucose or D-sorbitol metabolisation pathway such as, for example, D-glucose, D-sorbitol, L-sorbose, L-sorbosone, 2-keto-L-gulonate, D-gluconate, 2-keto-D-gluconate or 2,5-diketo-gluconate. A further possible substrate might be galactose. Preferably, the substrate is selected from for instance D-glucose, D-sorbitol, L-sorbose or L-sorbosone, more preferably from D-glucose, D-sorbitol or L-sorbose, and most preferably from D-sorbitol or L-sorbose. The term "substrate" and "production substrate" in connection with the above process using resting cells of a microorganism is used interchangeably herein.

Conversion of the substrate into vitamin C in connection with the above process using resting cells of a microorganism means that the conversion of the substrate resulting in vitamin C is performed by the microorganism, i.e. the substrate may be directly converted into vitamin C. Said microorganism is cultured under conditions which allow such conversion from the substrate as defined above.

A medium as used herein for the above process using resting cells of a microorganism may be any suitable medium for the production of vitamin C. Typically, the medium is an aqueous medium comprising for instance salts, substrate(s), and a certain pH. The medium in which the substrate is converted into vitamin C is also referred to as the production medium.

In connection with the above process using resting cells of a microorganism any microorganism capable of performing the conversion of the substrate to vitamin C may be used, such as for instance, yeast, algae or bacteria, either as wild type strains, mutant strains derived by classic mutagenesis and selection methods or as recombinant strains. Examples of such yeast may be, e.g., *Candida, Saccharomyces, Zygosaccharomyces, Scyzosaccharomyces*, or *Kluyveromyces*. An example of such algae may be, e.g., *Chlorella*. Examples of such bacteria may be, e.g., *Gluconobacter, Acetobacter, Ketogulonicigenium, Pantoea, Cryptococcus, Pseudomonas*, such as, e.g., *Pseudomonas putida*, and *Escherichia*, such as, e.g., *Escherichia coli*. Preferred are *Gluconobacter* or *Acetobacter aceti*, such as for instance *G. oxydans, G. cerinus, G. frateurii, A. aceti* subsp. *xylinum* or *A. aceti* subsp. *orleanus*.

In connection with the above process using resting cells of a microorganism the microorganisms which can be used for the present invention may be publicly available from different sources, e.g., Deutsche Sammlung von Mikroorganismen und Zellkulturen (DSMZ), Mascheroder Weg 1B, D-38124 Braunschweig, Germany, American Type Culture Collection (ATCC), P.O. Box 1549, Manassas, Va. 20108 USA on May 12, 2003 or Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Juso-honmachi 2-chome, Yodogawa-ku, Osaka 532-8686, Japan). Examples of preferred bacteria deposited with IFO are for instance *Gluconobacter oxydans* (formerly known as *G. melanogenus*) IFO 3293, *Gluconobacter oxydans* (formerly known as *G. melanogenus*) IFO 3292, *Gluconobacter oxydans* (formerly known as *G. rubiginosus*) IFO 3244, *Gluconobacter frateurii* (formerly known as *G. industrius*) IFO 3260, *Gluconobacter cerinus* IFO 3266, *Gluconobacter oxydans* IFO 3287, and *Acetobacter aceti* subsp. *orleanus* IFO 3259, which were all deposited on Apr. 5, 1954; *Acetobacter aceti* subsp. *xylinum* IFO 13693 deposited on Oct. 22, 1975, and *Acetobacter aceti* subsp. *xylinum* IFO 13773 deposited on Dec. 8, 1977. Strain *Acetobacter* sp. ATCC 15164, which is also an example of a preferred bacterium, was deposited with ATCC. Strain *Gluconobacter oxydans* (formerly known as *G. melanogenus*) N44-1 as another example of a preferred bacterium is a derivative of the strain IFO 3293 and is described in Sugisawa et al., Agric. Biol. Chem. 54: 1201-1209, 1990.

In connection with the above process using resting cells of a microorganism it is understood that the above-mentioned microorganisms also include synonyms or basonyms of such species having the same physiological properties, as defined by the International Code of Nomenclature of Prokaryotes. The nomenclature of the microorganisms as used herein is the one officially accepted (at the filing date of the priority application) by the International Committee on Systematics of Prokaryotes and the Bacteriology and Applied Microbiology Division of the International Union of Microbiological Societies, and published by its official publication vehicle International Journal of Systematic and Evolutionary Microbiology (IJSEM). A particular reference is made to Urbance et al., IJSEM (2001) vol 51:1059-1070, with a corrective notification on IJSEM (2001) vol 51:1231-1233, describing the taxonomically reclassification of *G. oxydans* DSM 4025 as *Ketogulonicigenium vulgare*.

As used herein, resting cells refer to cells of a microorganism which are for instance viable but not actively growing, or which are growing at low specific growth rates [μ], for instance, growth rates that are lower than $0.02\ h^{-1}$, preferably lower than $0.01\ h^{-1}$. Cells which show the above growth rates are said to be in a "resting cell mode".

The process of the present invention as above using resting cells of a microorganism may be performed in different steps or phases: preferably, the microorganism is cultured in a first step (also referred to as step (a) or growth phase) under conditions which enable growth. This phase is terminated by changing of the conditions such that the growth rate of the microorganism is reduced leading to resting cells, also referred to as step (b), followed by the production of vitamin C from the substrate using the resting cells of (b), also referred to as production phase.

Growth and production phase as performed in the above process using resting cells of a microorganism may be performed in the same vessel, i.e., only one vessel, or in two or more different vessels, with an optional cell separation step between the two phases. The produced vitamin C can be recovered from the cells by any suitable means. Recovering means for instance that the produced vitamin C may be separated from the production medium. Optionally, the thus produced vitamin C may be further processed.

For the purpose of the present invention relating to the above process using resting cells of a microorganism, the terms "growth phase", "growing step", "growth step" and "growth period" are used interchangeably herein. The same applies for the terms "production phase", "production step", "production period".

One way of performing the above process using resting cells of a microorganism as of the present invention may be a process wherein the microorganism is grown in a first vessel, the so-called growth vessel, as a source for the resting cells, and at least part of the cells are transferred to a second vessel, the so-called production vessel. The conditions in the production vessel may be such that the cells transferred from the growth vessel become resting cells as defined above. Vitamin C is produced in the second vessel and recovered therefrom.

In connection with the above process using resting cells of a microorganism, in one aspect, the growing step can be performed in an aqueous medium, i.e. the growth medium, supplemented with appropriate nutrients for growth under aerobic conditions. The cultivation may be conducted, for instance, in batch, fed-batch, semi-continuous or continuous mode. The cultivation period may vary depending on the kind of cells, pH, temperature and nutrient medium to be used, and may be for instance about 10 h to about 10 days, preferably about 1 to about 10 days, more preferably about 1 to about 5 days when run in batch or fed-batch mode, depending on the microorganism. If the cells are grown in continuous mode, the residence time may be for instance from about 2 to about 100 h, preferably from about 2 to about 50 h, depending on the microorganism. If the microorganism is selected from bacteria, the cultivation may be conducted for instance at a pH of about 3.0 to about 9.0, preferably about 4.0 to about 9.0, more preferably about 4.0 to about 8.0, even more preferably about 5.0 to about 8.0. If algae or yeast are used, the cultivation may be conducted, for instance, at a pH below about 7.0, preferably below about 6.0, more preferably below about 5.5, and most preferably below about 5.0. A suitable temperature range for carrying out the cultivation using bacteria may be for instance from about 13° C. to about 40° C., preferably from about 18° C. to about 37° C., more preferably from about 13° C. to about 36° C., and most preferably from about 18° C. to about 33° C. If algae or yeast are used, a suitable temperature range for carrying out the cultivation may be for instance from about 15° C. to about 40° C., preferably from about 20° C. to about 45° C., more preferably from about 25° C. to about 40° C., even more preferably from about 25° C. to about 38° C., and most preferably from about 30° C. to about 38° C. The culture medium for growth usually may contain such nutrients as assimilable carbon sources, e.g., glycerol, D-mannitol, D-sorbitol, L-sorbose, erythritol, ribitol, xylitol, arabitol, inositol, dulcitol, D-ribose, D-fructose, D-glucose, and sucrose, preferably L-sorbose, D-glucose, D-sorbitol, D-mannitol, and glycerol; and digestible nitrogen sources such as organic substances, e.g., peptone, yeast extract and amino acids. The media may be with or without urea and/or corn steep liquor and/or baker's yeast. Various inorganic substances may also be used as nitrogen sources, e.g., nitrates and ammonium salts. Furthermore, the growth medium usually may contain inorganic salts, e.g., magnesium sulfate, manganese sulfate, potassium phosphate, and calcium carbonate.

In connection with the above process using resting cells of a microorganism, in the growth phase the specific growth rates are for instance at least $0.02\ h^{-1}$. For cells growing in batch, fed-batch or semi-continuous mode, the growth rate depends on for instance the composition of the growth medium, pH, temperature, and the like. In general, the growth rates may be for instance in a range from about 0.05 to about $0.2\ h^{-1}$, preferably from about 0.06 to about $0.15\ h^{-1}$, and most preferably from about 0.07 to about $0.13\ h^{-1}$.

In another aspect of the above process using resting cells of a microorganism, resting cells may be provided by cultivation of the respective microorganism on agar plates thus serving as growth vessel, using essentially the same conditions, e.g., cultivation period, pH, temperature, nutrient medium as described above, with the addition of agar agar.

In connection with the above process using resting cells of a microorganism, if the growth and production phase are performed in two separate vessels, then the cells from the growth phase may be harvested or concentrated and transferred to a second vessel, the so-called production vessel. This vessel may contain an aqueous medium supplemented with any applicable production substrate that can be converted to L-ascorbic acid by the cells. Cells from the growth vessel can be harvested or concentrated by any suitable operation, such as for instance centrifugation, membrane crossflow ultrafiltration or microfiltration, filtration, decantation, flocculation. The cells thus obtained may also be transferred to the production vessel in the form of the original broth from the growth vessel, without being harvested, concentrated or washed, i.e. in the form of a cell suspension. In a preferred embodiment, the cells are transferred from the growth vessel to the production vessel in the form of a cell suspension without any washing or isolating step in-between.

Thus, in a preferred embodiment of the above process using resting cells of a microorganism step (a) and (c) of the process of the present invention as described above are not separated by any washing and/or separation step.

In connection with the above process using resting cells of a microorganism, if the growth and production phase are performed in the same vessel, cells may be grown under appropriate conditions to the desired cell density followed by a replacement of the growth medium with the production medium containing the production substrate. Such replacement may be, for instance, the feeding of production medium to the vessel at the same time and rate as the withdrawal or harvesting of supernatant from the vessel. To keep the resting cells in the vessel, operations for cell recycling or retention may be used, such as for instance cell recycling steps. Such recycling steps, for instance, include but are not limited to methods using centrifuges, filters, membrane crossflow microfiltration of ultrafiltration steps, membrane reactors, flocculation, or cell immobilization in appropriate porous, non-porous or polymeric matrixes. After a transition phase, the vessel is brought to process conditions under which the cells are in a resting cell mode as defined above, and the production substrate is efficiently converted into vitamin C.

The aqueous medium in the production vessel as used for the production step in connection with the above process using resting cells of a microorganism, hereinafter called production medium, may contain only the production substrate(s) to be converted into L-ascorbic acid, or may contain for instance additional inorganic salts, e.g., sodium chloride, calcium chloride, magnesium sulfate, manganese sulfate, potassium phosphate, calcium phosphate, and calcium carbonate. The production medium may also contain digestible nitrogen sources such as for instance organic substances, e.g., peptone, yeast extract, urea, amino acids, and corn steep liquor, and inorganic substances, e.g. ammonia, ammonium sulfate, and sodium nitrate, at such concentrations that the cells are kept in a resting cell mode as defined above. The medium may be with or without urea and/or corn steep liquor and/or baker's yeast. The production step may be conducted for instance in batch, fed-batch, semi-continuous or continuous mode. In case of fed-batch, semi-continuous or continuous mode, both cells from the growth vessel and production medium can be fed continuously or intermittently to the production vessel at appropriate feed rates. Alternatively, only production medium may be fed continuously or intermittently to the production vessel, while the cells coming from the growth vessel are transferred at once to the production vessel. The cells coming from the growth vessel may be used as a cell suspension within the production vessel or may be used as for instance flocculated or immobilized cells in any solid phase such as porous or polymeric matrixes. The production period, defined as the period elapsed between the entrance of the substrate into the production vessel and the harvest of the supernatant containing vitamin C, the so-called harvest stream, can vary depending for instance on the kind and concentration of cells, pH, temperature and nutrient medium to be used, and is preferably about 2 to about 100 h. The pH and temperature can be different from the pH and temperature of the growth step, but is essentially the same as for the growth step.

In a preferred embodiment of the above process using resting cells of a microorganism, the production step is conducted in continuous mode, meaning that a first feed stream containing the cells from the growth vessel and a second feed stream containing the substrate is fed continuously or intermittently to the production vessel. The first stream may either contain only the cells isolated/separated from the growth medium or a cell suspension, coming directly from the growth step, i.e. cells suspended in growth medium, without any intermediate step of cell separation, washing and/or isolating. The second feed stream as herein defined may include all other feed streams necessary for the operation of the production step, e.g. the production medium comprising the substrate in the form of one or several different streams, water for dilution, and base for pH control.

In connection with the above process using resting cells of a microorganism, when both streams are fed continuously, the ratio of the feed rate of the first stream to feed rate of the second stream may vary between about 0.01 and about 10, preferably between about 0.01 and about 5, most preferably between about 0.02 and about 2. This ratio is dependent on the concentration of cells and substrate in the first and second stream, respectively.

Another way of performing the process as above using resting cells of a microorganism of the present invention may be a process using a certain cell density of resting cells in the production vessel. The cell density is measured as absorbance units (optical density) at 600 nm by methods known to the skilled person. In a preferred embodiment, the cell density in the production step is at least about 10, more preferably between about 10 and about 200, even more preferably between about 15 and about 200, even more preferably between about 15 to about 120, and most preferably between about 20 and about 120.

In connection with the above process using resting cells of a microorganism, in order to keep the cells in the production vessel at the desired cell density during the production phase as performed, for instance, in continuous or semi-continuous mode, any means known in the art may be used, such as for instance cell recycling by centrifugation, filtration, membrane crossflow ultrafiltration of microfiltration, decantation, flocculation, cell retention in the vessel by membrane devices or cell immobilization. Further, in case the production step is performed in continuous or semi-continuous mode and cells are continuously or intermittently fed from the growth vessel, the cell density in the production vessel may be kept at a constant level by, for instance, harvesting an amount of cells from the production vessel corresponding to the amount of cells being fed from the growth vessel.

In connection with the above process using resting cells of a microorganism, the produced vitamin C contained in the so-called harvest stream is recovered/harvested from the production vessel. The harvest stream may include, for instance, cell-free or cell-containing aqueous solution coming from the production vessel, which contains vitamin C as a result of the conversion of production substrate by the resting cells in the production vessel. Cells still present in the harvest stream may be separated from the vitamin C by any operations known in the art, such as for instance filtration, centrifugation, decantation, membrane crossflow ultrafiltration or microfiltration, tangential flow ultrafiltration or microfiltration or dead end filtration. After this cell separation operation, the harvest stream is essentially free of cells.

In connection with the above process using resting cells of a microorganism, in one aspect, the process of the present invention leads to yields of vitamin C which are at least about 1.8 g/l, preferably at least about 2.5 g/l, more preferably at least about 4.0 g/l, and most preferably at least about 5.7 g/l. In one embodiment, the yield of vitamin C produced by the process of the present invention is in the range of from about 1.8 to about 600 g/l. The yield of vitamin C refers to the concentration of vitamin C in the harvest stream coming directly out of the production vessel, i.e. the cell-free supernatant comprising the vitamin C.

In connection with the above process using resting cells of a microorganism, in one embodiment of the present invention, vitamin C is produced by the process as described above using resting cells of recombinant microorganisms, such as for instance recombinant bacteria. Preferably, the recombinant bacteria are selected from bacteria that can express the L-sorbosone dehydrogenase as an active form in vivo, in particular bacteria of the genera *Gluconobacter, Acetobacter, Pseudomonas* and *Escherichia*, most preferred from *Gluconobacter, Acetobacter* or *E. coli*. Even more preferred are for instance *G. oxydans* and *E. coli* and the most preferred is selected from the group consisting of *G. oxydans* N44-1, *G. oxydans* IFO 3293 and *G. oxydans* IFO 3244. A recombinant microorganism may be any microorganism that is genetically engineered by well known techniques to contain one or more desired gene(s) on its chromosome or on a plasmid introduced into said microorganism, leading to, e.g., an overexpression of said gene(s). The desired gene(s) which are introduced into said microorganism may code for instance for an enzyme involved in the conversion of a substrate to vitamin C. In a preferred embodiment, the desired gene encodes an L-sorbosone dehydrogenase, catalyzing the conversion of L-sorbosone to vitamin C. A preferred L-sorbosone dehydrogenase as used in the present invention is for instance the L-sorbosone dehydrogenase (SNDHai) of *G. oxydans* N44-1 (Sugisawa et al., Agric. Biol. Chem. 54: 1201-1209, 1990) as represented by SEQ ID NO:2, the nucleotide sequence encoding said SNDHai is represented by SEQ ID NO:1. Functional derivatives of said SNDHai can also be used for the purpose of the present invention. It is understood that nucleotide sequences having a homology of at least 80%, preferably of at least 90%, compared with SEQ ID NO:1 and which code for enzymes able to catalyze the conversion of L-sorbosone to vitamin C are also part of the present invention.

The recombinant microorganism, such as for example *G. oxydans* N44-1, may comprise several copies of SNDHai cloned on a suitable plasmid or integrated on its chromosome. Plasmid copies which may be suitable for the present invention are for instance in the range of about 2 to about 15, preferably in the range of about 5 to about 10 per transformed microorganism. The number of plasmid copies may be determined by, for instance, comparison of the intensity of a respective band visible on SDS-PAGE.

In connection with the above process using resting cells of a microorganism, when using recombinant microorganisms for the process of the present invention, the growth and production step can be essentially the same as described above. If a recombinant microorganism comprising SNDHai is used, such as for example recombinant *G. oxydans* N44-1 with increased SNDHai dosage, the growth medium may contain for instance D-sorbitol, L-sorbose, glycerol or D-glucose either alone or mixtures thereof, one or more suitable nitrogen sources and salts. The production medium may contain for instance D-sorbitol and/or L-sorbose and salts. Harvesting of vitamin C can be performed as essentially described herein.

In a further aspect, the process of the present invention may be combined with further steps of separation and/or purification of the produced vitamin C from other components contained in the harvest stream, i.e., so-called downstream processing steps. These steps may include any means known to a skilled person, such as, for instance, concentration, crystallization, precipitation, adsorption, ion exchange, electrodialysis, bipolar membrane electrodialysis and/or reverse osmosis. Vitamin C may be further purified as the free acid form or any of its known salt forms by means of operations such as for instance treatment with activated carbon, ion exchange, adsorption and elution, concentration, crystallization, filtration and drying. Specifically, a first separation of vitamin C from other components in the harvest stream might be performed by any suitable combination or repetition of, for instance, the following methods: two- or three-compartment electrodialysis, bipolar membrane electrodialysis, reverse osmosis or adsorption on, for instance, ion exchange resins or non-ionic resins. If the resulting form of vitamin C is a salt of L-ascorbic acid, conversion of the salt form into the free acid form may be performed by for instance bipolar membrane electrodialysis, ion exchange, simulated moving bed chromatographic techniques, and the like. Combination of the mentioned steps, e.g., electrodialysis and bipolar membrane electrodialysis into one step might be also used as well as combination of the mentioned steps e.g. several steps of ion exchange by using simulated moving bed chromatographic methods. Any of these procedures alone or in combination constitute a convenient means for isolating and purifying the product, i.e. vitamin C. The product thus obtained may further be isolated in a manner such as, e.g. by concentration, crystallization, precipitation, washing and drying of the crystals and/or further purified by, for instance, treatment with activated carbon, ion exchange and/or re-crystallization.

In a preferred embodiment, vitamin C is purified from the harvest stream by a series of downstream processing steps as described above without having to be transferred to a non-aqueous solution at any time of this processing, i.e. all steps are performed in an aqueous environment. Such preferred downstream processing procedure may include for instance the concentration of the harvest stream coming from the production vessel by means of two- or three-compartment electrodialysis, conversion of vitamin C in its salt form present in the concentrated solution into its acid form by means of bipolar membrane electrodialysis and/or ion exchange, purification by methods such as for instance treatment with activated carbon, ion exchange or non-ionic resins, followed by a further concentration step and crystallization. These crystals can be separated, washed and dried. If necessary, the crystals may be again re-solubilized in water, treated with activated carbon and/or ion exchange resins and recrystallized. These crystals can then be separated, washed and dried.

The following Examples further illustrate the present invention and are not intended to limit the invention in any way.

EXAMPLE 1

L-Ascorbic Acid Production with Purified SNDHai

1. Purification of SNDHai:

Cells of a microorganism capable of producing SNDHai cultivated by fed-batch fermentation (for cultivation see Example 3) were suspended in 25 ml of phosphate buffer (20 mM, pH 7.0) containing $MgCl_2$, 2 mM, dithiothreitol (DTT), 1 mM, and 2-3 EDTA-free protease inhibitor tablets (Roche Diagnostics GmbH). The cell suspension was treated three times with a French Pressure cell. Subsequently, 25 ml of phosphate buffer (20 mM, pH 7.0) containing 2 mM $MgCl_2$ and 1 M NaCl were added and the suspension was ultracentrifuged (30.000 rpm, 60 min, 4° C.). The pellet containing the membrane fraction was washed with phosphate buffer (20 mM, pH 7.0) containing 2 mM $MgCl_2$ and 500 mM NaCl and then suspended in an appropriate amount of phosphate buffer (20 mM, pH 7.0) containing 2 mM $MgCl_2$. N-Octylglucoside (Fluka) was then added at a final concentration of 2% (w/v) and the suspension was incubated for 90 min with gentle stirring on ice. After centrifugation (20.000 rpm, 60 min, 4° C.) the clear reddish supernatant was collected and polyethylene glycol 6000 (Fluka) at a final concentration of 15% (w/v) was added. After incubation for 60 min at 4° C. with gentle shaking followed by centrifugation (10.000 rpm, 30 min, 4° C.), the pellet was dissolved in Tris-HCl buffer (20 mM, pH 7.6) containing 2 mM $MgCl_2$ and 0.5% (w/v) lauryl sulfobetaine (Fluka). After gentle shaking at 4° C. overnight the solution was centrifuged (20.000 rpm, 30 min, 4° C.). The supernatant was collected and further purified as follows.

The following purification steps were done at 4° C. on an A=A Explorer 10 S-system (Amersham Biosciences) with software UNICORN 3.1. Typical flow rates for ion exchange chromatography were in the range of 1-2 ml/min. Protein elution was monitored at 280 nm and SNDHai-active fractions were determined using the standard photometric assay at all stages of the purification (s. below) or the product assay with purified fractions.

The clear supernatant IV was desalted in 2.5 ml-portions on a Sephadex G 25-gel filtration column (void volume: 2.5 ml) using 20 mM Tris-HCl buffer (pH 7.6) containing 2 mM $MgCl_2$ and 0.5% (w/v) lauryl sulfobetaine.

SNDHai-positive fractions were pooled and an aliquot (approximately 10 ml) was put on a strong anion exchange column (e.g. Mono-Q HR, Amersham Biosciences, column volume: 8 ml) which had been equilibrated prior to use with buffer A1 (10 mM Tris, 10 mM BisTris, 10 mM MES, 2 mM $MgCl_2$, 0.5% lauryl sulfobetaine, pH 7.6). Non-binding proteins were eluted with 100% buffer A1 and after 4 column volumes a linear pH-gradient in 6 column volumes to 100% buffer B1 (Tris, 10 mM; BisTris, 10 mM; MES, 10 mM; $MgCl_2$, 2 mM, and lauryl sulfobetaine, 0.5%, pH 4.7) was applied followed by 8 column volumes of 100% buffer B1. SNDHai eluted at a pH-value of approximately 6.5, which is very close to the pI-value of 6.52 calculated from the amino acid sequence. Active fractions were pooled, diluted with the same amount of HEPES-buffer (50 mM, pH 8.0) containing 2 mM $MgCl_2$ and 0.5% lauryl sulfobetaine (final volume: 15-20 ml), and applied to another strong anion exchange column (e.g. Mono-Q HR, Amersham Biosciences, column volume: 1 ml) which had been equilibrated with buffer A2 (15 mM HEPES, 2 mM $MgCl_2$, 0.5% lauryl sulfobetaine, pH 7.6). Non-binding proteins were eluted with 100% buffer A2 and after 4 column volumes a linear salt-gradient in 20 column volumes to 40% buffer B2 (HEPES, 15 mM; $MgCl_2$, 2 mM, LiCl, 1 M, and lauryl sulfobetaine, 0.5%, pH 7.6) was applied followed by a step gradient to 100% buffer B2. SNDHai eluted around 150 mM LiCl. Active fractions showed one single band at approximately 85 kDa in SDS gel electrophoresis.

2. Photometric Assay for SNDHai.

The reaction mixture for the photometric SNDHai-activity measurement consisted of 0.196 mM nitroblue tetrazolium chloride (NBT), 0.137 mM phenazine methosulfate (PMS), 20.4 mM L-sorbosone, and enzyme solution in a final volume of 1.0 ml of 0.1 M sodium phosphate buffer, pH 7.5. The reaction was started with the addition of enzyme, and the enzyme activity was measured in a cuvette with 1-cm light path as the initial reduction rate of NBT at 570 nm (T=25° C.). One unit of the enzyme activity was defined as the amount of enzyme catalyzing the reduction of 1 µM NBT per minute. The extinction coefficient of NBT at pH 7.5 was taken as 100 $mM^{-1}$ $cm^{-1}$. Two kinds of reference cuvettes were used for the activity determination: one contained the above-mentioned components except for L-sorbosone and another one contained all components except for the enzyme solution.

3. Product Assay for SNDHai.

Pure SNDHai-containing fractions (see above) were analyzed directly for L-ascorbic acid production from L-sorbosone with an assay of the following composition (0.5 ml total volume): 0.14 mg/ml of purified and desalted SNDHai, 50 mM phosphate buffer (pH 6.5), 8 mg/ml bovine serum albumin (BSA), 100 mM L-sorbosone, 1 mM PMS, 5 mM $CaCl_2$, 50 µM $PQQ-K_2$. The assay was conducted in appropriate reaction tubes at 25° C. with sufficient shaking (900 rpm on a benchtop shaker) under exclusion of light.

Samples were analyzed by high performance liquid chromatography (HPLC) using an Agilent 1100 HPLC system (Agilent Technologies, Wilmington, USA) with a LiChrospher-100-RP18 (125×4.6 mm) column (Merck, Darmstadt, Germany) attached to an Aminex-HPX-78H (300×7.8 mm) column (Biorad, Reinach, Switzerland). The mobile phase was 0.004 M sulfuric acid, and the flow rate was 0.6 ml/min. Two signals were recorded using a UV detector (wavelength 254 nm) in combination with a refractive index detector. In addition, the identification of the L-ascorbic acid was done using an amino-column (YMC-Pack Polyamine-II, YMC, Inc., Kyoto, Japan) with UV detection at 254 nm. The mobile phase was 50 mM $NH_4H_2PO_4$ and acetonitrile (40:60). Typical initial volumetric L-ascorbic acid-productivities under these conditions were 0.5-1.0 g/l/h. Thus, after 1 h reaction time, the concentration of L-ascorbic acid in the supernatant was 300 to 930 mg/l.

EXAMPLE 2

L-Ascorbic Acid Production from L-Sorbose and D-Sorbitol in Tube and Flask Fermentations Cells of *G. oxydans* N44-1 were used to inoculate 4 ml of No. 3BD liquid medium and cultivated in a tube (18 mm diameter) at 30° C. for 3 days with shaking at 220 rpm. 20 mg/l of L-ascorbic acid had accumulated at the end of the incubation period.

Cells of strain N44-1 were cultivated (in triplicate) in 50 ml of No. 5 medium containing 100 g/l D-sorbitol, 0.5 g/l glycerol, 15 g/l yeast extract (Difco), 2.5 g/l of $MgSO_4.7H_2O$, and 15 g/L of $CaCO_3$ in a 500 ml baffled shake flask at 30° C. with shaking at 200 rpm. After 72 h of cultivation, the amounts of L-ascorbic acid measured by HPLC in the three flasks were 400, 500 and 680 mg/l.

EXAMPLE 3

L-Ascorbic Acid Production from D-Sorbitol in Fed-Batch Fermentation

Cells of *G. oxydans* N44-1 were grown in 200 ml No. 5 medium containing 100 g/l D-sorbitol, 0.5 g/l glycerol, 15 g/l yeast extract (Fluka BioChemika, Buchs, Switzerland), 2.5 g/l $MgSO_4.7H_2O$ and 15 g/l $CaCO_3$ in a 2-l baffled shake flask at 30° C. with shaking at 180 rpm. After 48 h, 150 ml of this culture was used to inoculate a 10-l bioreactor (B. Braun ED10, Melsungen, Germany) previously prepared with 5.3 l medium containing 20 g/l D-sorbitol, 0.5 g/l glycerol, 15 g/l yeast extract (Fluka BioChemika, Buchs, Switzerland) and 2.5 g/l $MgSO_4.7H_2O$ and equipped with temperature, pH and dissolved oxygen sensors and control loops. Temperature was controlled at 30° C., pH was controlled at 6.0 by adding a 28% ammonia solution, airflow was 4.5/min and dissolved oxygen was controlled at 30% by a cascade with stirring speed (minimum 300 rpm). After 6 h process time, a 500 g/l sorbitol solution was fed at a rate of 25 g/h for a period of 44 h. After 96 h process time, about 1% substrate was left in the supernatant, and 950 mg/l L-ascorbic acid had been produced.

EXAMPLE 4

L-Ascorbic Acid Production from L-Sorbosone or L-Sorbose with a Cell Membrane Fraction Cells of *G. oxydans* N44-1 were cultivated in 100 ml of No. 3BD liquid medium in a 500 ml baffled shake flask at 30° C. with shaking at 220 rpm for 3 days. The resulting culture was centrifuged at 500 rpm to remove $CaCO_3$. The supernatant from this step was then centrifuged at 5,000 rpm to pellet the cells. The collected cells were suspended in 3 ml of 50 mM potassium phosphate buffer (pH7.0) and the cells were disrupted by two passages through a French Pressure cell (SIM-AMINCO Spetronic Instruments, USA) at 900 psi. The resulting homogenate was first centrifuged at 5,000 rpm to remove cell debris. Then the supernatant was diluted to a final protein concentration of 3 mg of protein/ml. This diluted sample is designated as cell-free extract (CFE). The CFE was centrifuged at 100,000×g for 60 min. The supernatant was discarded and the pellet was collected as the membrane fraction.

The reaction (200 µl) with the membrane fraction (100 µl) was carried out in 50 mM potassium phosphate buffer (pH7.0), 30° C. with shaking at 220 rpm for 15 h. The substrates tested were L-sorbosone (1% final concentration) and L-sorbose (2% final concentration). The final protein concentration used in the reaction was 1.5 mg/ml. At the end of the incubation period, 680 mg/l and 10 mg/l of L-ascorbic acid had been produced from 1% L-sorbosone and 2% L-sorbose, respectively.

EXAMPLE 5

Isolation of the SNDHai Gene from *Gluconobacter oxydans* N44-1

1. Tn5 Mutagenesis

Plasmid pSUP2021, a "suicide" vector containing Tn5 (Simon R. et al. 1983. BIO/TECHNOLOGY 1: 784-791), was transferred from *E. coli* HB101 into *G. oxydans* N44-1 by a conjugal mating method as follows. *G. oxydans* N44-1 was cultivated in a test tube containing 5 ml of MB liquid medium at 30° C. overnight. *E. coli* HB101 carrying helper plasmid pRK2013 (D. H. Figurski, Proc. Natl. Acad. Sci. USA, 76, 1648-1652, 1979) and *E. coli* HB101 carrying plasmid pSUP2021 were cultivated in test tubes containing 5 ml of LB medium with 50 µg/ml of kanamycin at 37° C. overnight. From the overnight cultures, cells of *G. oxydans* N44-1, *E. coli* HB101 (pRK2013), and *E. coli* HB101 (pSUP2021) were collected separately by centrifugation and suspended to the original volume in MB medium. Then these cell suspensions were mixed in equal volumes and the mixture was spread out on a 0.45 µm nitrocellulose membrane laid on top of an MB agar plate. After cultivation at 27° C. for one day, the cells were scraped off the membrane and dilutions were prepared in MB broth. The diluted cells were then spread on MB agar medium containing 10 µg/ml of polymixin B and 50 µg/ml of kanamycin (MPK medium). The polymixin B selects against the *E. coli* donor and helper strains, while the kanamycin selects for those *G. oxydans* cells that have been transformed with plasmid pSUP2021 (i.e., the transconjugants). About 30,000 transconjugants were obtained.

2. Screening for L-Ascorbic Acid Non-Producers.

In all, 3,760 transconjugants were transferred with sterile toothpicks onto MPK grid plates and grown at 27° C. for 3 days. To test for L-ascorbic acid production from L-sorbosone, cells of each transconjugant were picked off the grid plate with a sterile toothpick and suspended in 50 µl of a resting cell reaction mixture containing 0.5% L-sorbosone, 0.3% NaCl, and 1% $CaCO_3$ in 96-well microtiter plates. The microtiter plates were incubated at 30° C. for one day without shaking. One microliter of each of the resulting reaction mixtures was analyzed for L-ascorbic acid formation using ascorbic acid test strips and the RQFlex2 instrument (Merck KGBA, 64271 Darmstadt, Germany). The positive control strain was *G. oxydans* N44-1 grown under identical conditions. By this method, the L-ascorbic acid-non-producing mutant N44-1-6A9 was identified. Southern blot hybridization analysis was then performed to confirm the presence of Tn5 in the chromosomal DNA of mutant N44-1-6A9. 2 µg of chromosomal DNA isolated from the mutant was digested with either ApaI, ClaI, EcoRI, EcoRV, KpnI, StuI, BamHI, SalI, or HindIII and subjected to agarose gel electrophoresis (0.8% agarose). The gel was then treated with 0.25 N HCl for 15 min, followed by 0.5 N NaOH for 30 min. The DNA was transferred to a nylon membrane with the rapid downward transfer system TurboBlotter (Schleicher & Schuell GmbH, Germany). The probe was prepared with PCR-DIG labeling kit (Roche Diagnostics GmbH, 68298 Mannheim, Germany) using primers Tn2419 (SEQ ID NO:3) and Tn3125R (SEQ ID NO:4) with plasmid pSUP2021 as the template. A 707-bp PCR product was obtained.

The hybridization conditions used were as follows: hybridization was done under stringent hybridization conditions, e.g., 2 hours to 4 days incubation at 42° C. using a digoxigenin (DIG)-labeled DNA probe (prepared by using a DIG labeling system; Roche Diagnostics GmbH, 68298 Mannheim, Germany) in DigEasyHyb solution (Roche Diagnostics) with 100 µg/ml salmon sperm DNA, followed by washing the filters for 15 min (twice) in 2×SSC and 0.1% SDS at room temperature and then washing for 15 min (twice) in 0.5×SSC and 0.1% SDS or 0.1×SSC and 0.1% SDS at 65° C.

Following the hybridization step, the detection of hybridization was done with anti-DIG-AP conjugate (Roche Diagnostics GmbH, 68298 Mannheim, Germany) and ECF substrate (Amersham Biosciences Uppsala, Sweden) using the STORM instrument (Amersham Biosciences). All operations were done according to the instructions of the suppliers.

Using the methods described above, the presence of Tn5 in the chromosome of mutant N44-1-6A9 was confirmed.

3. Cloning of a DNA Fragment Interrupted by Tn5 and Sequencing of the Adjacent Regions.

Based on the results of the restriction enzyme digestions described in section 2 above, ApaI, ClaI, EcoRI, and EcoRV were selected as the enzymes that generated DNA fragments having more than 1 kb of flanking chromosomal DNA at both sides of the Tn5 insertion. Double digestion of mutant N44-1-6A9 DNA with SalI (which cuts approximately in the middle of Tn5) and ApaI gave two fragments (6.2 and 3.8 kb) that hybridized to the 707-bp probe described above.

The chromosomal DNA of the Tn5 mutant *G. oxydans* N44-1-6A9 was prepared and digested with ApaI. The DNA fragments with the size of from 9 to 12 kb were isolated from agarose gel and ligated with the cloning vector pBluescript II KS+ (Stratagene, Switzerland), previously digested with ApaI. The ligation mixture was then used to transform competent *E. coli* cells, selecting on L-agar plates containing 50 µg/ml kanamycin and 100 µg/ml ampicillin. From one transformant, the plasmid was extracted and the cloned regions flanking the Tn5 insertion were sequenced. The nucleotide sequence of the single open reading frame (interrupted by the Tn5 insertion) was assembled after removing a 9-bp duplication that is known to occur during the Tn5 transposition event. The nucleotide sequence of the full open reading frame, hereafter referred to as the SNDHai gene of *Gluconobacter oxydans* N44-1, consisted of 2367 bp and is given as SEQ ID NO:1. The corresponding amino acid sequence deduced from the nucleotide sequence of SEQ ID NO:1 is given here as SEQ ID NO:2.

The nucleotide sequence of the SNDHai gene (SEQ ID NO:1) was subjected to a Blast 2 search (version 2 of BLAST from the National Center for Biotechnology Information [NCBI] described in Altschul et al. (Nucleic Acids Res. 25: 3389-3402, 1997)) on the database PRO SW-SwissProt (full release plus incremental updates). The conditions used were the gapped alignment and filtration of the query sequence for the low complexity region.

Using the program MOTIFS, bacterial quinoprotein dehydrogenases signature sequences were readily identified, indicating that SNDHai has the characteristics of a PQQ-dependent enzyme.

EXAMPLE 6

Southern Blot Analysis of the Bacteria Producing L-Ascorbic Acid from L-Sorbosone Chromosomal DNA was prepared from cells of *Gluconobacter oxydans* IFO 3293, IFO 3292, IFO 3244, IFO 3287, *Gluconobacter frateurii* IFO 3260 and IFO 3265, *Gluconobacter cerinus* IFO 3266 and IFO 3269, *Acetobacter aceti* subsp. *orleanus* IFO 3259, *Acetobacter aceti* subsp. *xylinum* IFO 13693 and IFO 13773, *Acetobacter* sp. ATCC 15164, and *Escherichia coli* K-12. Strains IFO 13693 and IFO 13773 were grown at 27° C. for 3 days on No. 350 medium containing 5 g/l Bactopeptone (Difco), 5 g/L yeast extract (Difco), 5 g/L glucose, 5 g/L mannitol, 1 g/L $MgSO_4.7H_2O$, 5 ml/L ethanol, and 15 g/L agar. All other *Acetobacter* strains and all *Gluconobacter* strains were grown at 27° C. for 3 days on mannitol broth (MB) agar medium containing 25 g/l mannitol, 5 g/l yeast extract (Difco Laboratories, Detroit, Mich., USA), 3 g/l Bactopeptone (Difco), and 18 g/l of agar (Difco). *E. coli* K-12 was grown on Luria Broth agar medium. The chromosomal DNA preparations were used for Southern blot hybridization under stringent conditions as described in Example 5. The chromosomal DNA preparations were digested with ClaI (when analyzing the N-domain region) or EcoRI (when analyzing the C-domain region), and 1 μg of the DNA fragments were separated by agarose gel electrophoresis (1% agarose). The gel was treated with 0.25 N HCl for 15 min and then 0.5 N NaOH for 30 min, and then was blotted onto a nylon membrane with Vacuum Blotter Model 785 (BIO-RAD Laboratories AG, Switzerland) according to the instruction of the supplier. The probes were prepared with PCR-DIG labeling kit (Roche Diagnostics) by using the primer sets as described in Table 2. The PCR product P1 corresponds to the region of SNDHai designated the N-domain (possible transmembrane region) while PCR product P2 corresponds to the region of SNDHai designated as the C-domain (possible primary dehydrogenase region).

TABLE 2

Primers used for PCR to generate labeled probes for Southern hybridizations

| Primer set | SEQ ID NOs. of primers | PCR product | Expected size of PCR product (bp) |
|---|---|---|---|
| SNDH1F and SNDH420R | 5 and 6 | P1 | 420 |
| SNDH501F and SNDH2364R | 7 and 8 | P2 | 1864 |
| SNDH501F and SNDH1530R | 7 and 9 | P3 | 1030 |
| SNDH1391F and SNDH2364R | 10 and 8 | P4 | 974 |

Table 2 shows the results of the Southern blot hybridization experiments. In the hybridization with the P1 (N-domain) probe, clear positive bands were observed for G. oxydans IFO 3293, IFO 3292, IFO 3244, IFO 3287 and A. sp. ATCC 15164. In the hybridization with the P2 (C-domain) probe, clear positive bands were observed for strains IFO 3293, IFO 3292, IFO 3244, IFO 3287 and A. sp. ATCC 15164, while a faint band was observed for stains IFO 3260, IFO 3265, IFO 3266, IFO 3269 and IFO 13773. The control strain, E. coli K-12, showed no detectable signals for either domain.

TABLE 3

Detection of hybridization signals in different strains obtained by Southern blot hybridization with probes for N- and C-domains of SNDHai (probes P1 and P2)

| Strain | P1 | P2 |
|---|---|---|
| G. oxydans IFO 3293 | + | + |
| G. oxydans IFO 3292 | + | + |
| G. oxydans IFO 3244 | + | + |
| G. frateurii IFO 3260 | nd | tr |
| G. frateurii IFO 3265 | nd | tr |
| G. cerinus IFO 3266 | nd | tr |
| G. oxydans IFO 3269 | nd | tr |
| G. oxydans IFO 3287 | + | + |
| A. aceti subsp. orleanus IFO 3259 | nd | nd |
| A. aceti subsp. xylinum IFO 13693 | nd | nd |
| A. aceti subsp. xylinum IFO 13773 | nd | tr |
| Acetobacter sp. ATCC 15164 | + | + |
| E. coli K-12 | nd | nd |

Tr, trace; nd, not detected. Probes P1 and P2 were synthesized (as DIG-labeled PCR products) with the primer sets specified in Table 2.

EXAMPLE 7

PCR Amplification and Sequencing of Orthologs of the Gluconobacter oxydans N44-1 SNDHai Gene Chromosomal DNA preparations (prepared as described in Example 6) were used as templates for PCR with the four primer sets shown in Table 2. Five to 100 ng of chromosomal DNA was used per reaction (total volume, 50 μl). Unless specified otherwise, the Expand High Fidelity PCR system was used (Roche Diagnostics). The PCR conditions were as follows:

Incubation at 94° C. for 2 min; 30 cycles of (i) denaturation step at 94° C. for 15 sec, (ii) annealing step at 60° C. for 30 sec. (iii) synthesis step at 72° C. for 45 to 120 sec (time for the synthesis step for primer sets P1, P2, P3 and P4 were 45 sec, 120 sec. 90 sec, and 90 sec, respectively); extension at 72° C. for 7 min.

Samples of the PCR reactions were separated by agarose gel electrophoresis and the bands were visualized with a transilluminator after staining with ethidium bromide. The results of the PCR reactions are summarized in Table 4.

TABLE 4

Detection of PCR products P1, P2, P3 and P4 in different strains obtained with the primer sets of Table 2 (products visualized via agarose gel electrophoresis)

| Strain | P1 | P2 | P3 | P4 |
|---|---|---|---|---|
| G. oxydans IFO 3293 | + | +* | nt | + |
| G. oxydans IFO 3292 | + | nd | nd | + |
| G. oxydans IFO 3244 | + | + | + | + |
| G. frateurii IFO 3260 | nd | nd | nd | nd |
| G. cerinus IFO 3266 | nd | nd | nd | nd |
| G. oxydans IFO 3287 | + | + | nd | + |
| A. aceti subsp. orleanus IFO 3259 | nd | nd | nd | nd |
| A. aceti subsp. xylinum IFO 13693 | nd | nd | nd | nd |
| A. aceti subsp. xylinum IFO 13773 | nd | nd | nd | nd |
| Acetobacter sp, ATCC 15164 | + | + | nd | nd |
| E. coli K-12 | nd | nd | nt | nd |

+, detected; nd, not detected; nt, not tested.
*This PCR was done with GC-rich PCR system (Roche Diagnostics) with the same reaction cycle as was used for Expand High Fidelity PCR system.

When clear PCR bands were observed on the agarose gel (Table 4), the PCR products were used directly for nucleotide sequencing using standard methods. The nucleotide sequences obtained for the different PCR products, and the corresponding amino acid sequences of the encoded peptides, were compared with the full length sequence of the SNDHai gene and protein from G. oxydans N44-1.

Gluconobacter oxydans IFO 3292 SNDHai Ortholog

The PCR product (about 1 kb) obtained upon amplification with primers SNDH1391F (SEQ ID NO:10) and SNDH2364R (SEQ ID NO:8) and chromosomal DNA from G. oxydans IFO 3292 as the template, was used for sequencing with primer SNDH1391F (SEQ ID NO:10). The determined nucleotide sequence of 771 bp (SEQ ID NO:11) showed 98.7% (761/771) homology with nucleotides 1431-2201 of the sequence of SNDHai from G. oxydans N44-1 (SEQ ID NO:1). The deduced amino acid sequence of 256 amino acids (SEQ ID NO:12) showed 100% identity to amino acids 478-733 of the amino acid sequence of SNDH from G. oxydans N44-1 (SEQ ID NO:2).

Gluconobacter oxydans IFO 3287 SNDHai Ortholog

The PCR product (about 0.4 kb) obtained upon amplification with primers SNDH1F (SEQ ID NO:5) and SNDH420R (SEQ ID NO:6) and chromosomal DNA from *G. oxydans* IFO 3287 as the template, was used for sequencing with primer SNDH420R (SEQ ID NO:6). The determined nucleotide sequence of 350 bp (SEQ ID NO:13) showed 97.4% (341/350) homology with nucleotides 31-380 of SEQ ID NO:1. The deduced amino acid sequence of 116 residues (SEQ ID NO:14) showed 100% identity with amino acids 11-126 of SEQ ID NO:2.

The PCR product (about 1.9 kb) obtained upon amplification with primers SNDH501F (SEQ ID NO:7) and SNDH2364R (SEQ ID NO:8) was used for sequencing with primer SNDH501F (SEQ ID NO:7). The determined nucleotide sequence of 808 bp (SEQ ID NO:15) showed 98.0% (745/808) homology with nucleotides 578-1385 of SEQ ID NO:1. The deduced amino acid sequence of 268 residues (SEQ ID NO:16) showed 100% identity to amino acids 194-461 of SEQ ID NO:2.

The PCR product (about 1 kb) obtained upon amplification with primers SNDH1391F (SEQ ID NO:10) and SNDH2364R (SEQ ID NO:8) was used for sequencing with primer SNDH1391F (SEQ ID NO:10). The determined nucleotide sequence of 800 bp (SEQ ID NO:17) showed 98.8% (790/800) homology with nucleotides 1469-2268 of SEQ ID NO:1. The deduced amino acid sequence of 266 residues (SEQ ID NO:18) showed 100% identity with amino acids 491-756 of SEQ ID NO:2.

*Acetobacter* sp. ATCC 15164 SNDHai Ortholog

The PCR product (about 0.4 kb) obtained upon amplification with primers SNDH1F (SEQ ID NO:5) and SNDH420R (SEQ ID NO:6) and chromosomal DNA from *A.* sp. ATCC 15164 as the template, was used for sequencing with primer SNDH420R (SEQ ID NO:6). The determined nucleotide sequence of 360 bp (SEQ ID NO:19) showed 97.8% (352/360) homology with nucleotides 31-390 of SEQ ID NO:1. The deduced amino acid sequence of 120 residues (SEQ ID NO:20) showed 100% identity with amino acids 11-130 of SEQ ID NO:2.

The PCR product (about 1.9 kb) obtained upon amplification with primers SNDH501F (SEQ ID NO:7) and SNDH2364R (SEQ ID NO:8) was used for sequencing with primer SNDH501F (SEQ ID NO:7). The determined nucleotide sequence of 760 bp (SEQ ID NO:21) showed 98.0% (745/760) homology with nucleotides 563-1322 of SEQ ID NO:1. The deduced amino acid sequence of 252 residues (SEQ ID NO:22) showed 100% identity with amino acids 189-440 of SEQ ID NO:2.

*Gluconobacter oxydans* IFO 3244 SNDHai Ortholog

Complete nucleotide sequence of the SNDHai ortholog gene of *G. oxydans* IFO 3244 was determined by using the PCR products obtained with the chromosomal DNA of *G. oxydans* IFO 3244 as the template and the following primer sets: SNDH1F (SEQ ID NO:5) and SNDH420R (SEQ ID NO:6); SNDH501F (SEQ ID NO:7) and SNDH1530R (SEQ ID NO:9); SNDH1391P (SEQ ID NO:10) and SNDH2364R (SEQ ID NO:8); SNDH382 (SEQ ID NO:23) and SNDH1530R (SEQ ID NO:9); SNDH1F (SEQ ID NO:5) and SNDH689R (SEQ ID NO:24). Chromosomal DNA digested with BglII and BamHI and ligated was used for two more PCRs with following primer sets: SNDH420R (SEQ ID NO:6) and SNDH501F (SEQ ID NO:7) and SNDH1530R (SEQ ID NO:9) and IS-50.3 (SEQ ID NO:25). The complete nucleotide sequence (SEQ ID NO:26) showed 98.4% homology to the nucleotide sequence of SNDHai from *G. oxydans* N44-1 (SEQ ID NO:1). The deduced amino acid sequence (SEQ ID NO:27) showed 100% identity to the amino acid sequence of SEQ ID NO:2.

EXAMPLE 8

Increased L-Ascorbic Acid Production from L-Sorbosone by Increasing the SNDHai Gene Dosage The SNDHai gene with upstream and downstream flanking regions was amplified by PCR with chromosomal DNA of strain N44-1 as template and the primer set N1 (SEQ ID NO:28) and N2 (SEQ ID NO:29).

The PCR was done with the GC-rich PCR system (Roche Diagnostics) according to the instructions of the supplier. The amplified DNA fragment was inserted into vector pCR2.1-TOPO (Invitrogen, Carlsbad, Calif., USA). The resulting plasmid was then digested with HindIII and XhoI. The HindIII-XhoI fragment including the SNDHai gene was ligated to vector pVK100 (available from the American Type Culture Collection, catalog no. ATCC 37156) previously treated with HindIII and XhoI. The ligation mixture was used to transform *E. coli* TG1. The desired plasmid, designated pVK-P-SNDHai-T, was isolated from *E. coli*, and introduced into *G. oxydans* strain N44-1 by electroporation using standard methods (Electrocell manipulator ECM600, BTX Inc., San Diego, Calif., USA).

Cells of *G. oxydans* strains N44-1 and N44-1 carrying the plasmid pVK-P-SNDHai-T were cultivated in 50 ml of No. 5 medium containing 100 g/l D-sorbitol, 0.5 g/l glycerol, 15 g/l yeast extract (Difco), 2.5 g/l of $MgSO_4.7H_2O$, and 15 g/L of $CaCO_3$ in a 500 ml baffled shake flask at 30° C. with shaking at 200 rpm. After 48 h of cultivation, the amounts of L-ascorbic acid measured in the supernatant by HPLC in the two flasks were 110 mg/l and 200 mg/l, respectively.

EXAMPLE 9

Production of L-Ascorbic Acid from L-Sorbosone Using Resting Cells Grown on Mannitol Broth Agar Medium IFO strains 3293, 3292, 3244, 3260, 3266, 3287, 3259, 13693, and 13773 as well as *Acetobacter* sp. ATCC 15164 and *Gluconobacter oxydans* N44-1, a derivative of the strain IFO 3293, were used for the production of L-ascorbic acid from L-sorbosone.

Strains IFO 13693 and IFO 13773 were grown at 27° C. for 3 days on No. 350 medium containing 5 g/l Bactopeptone (Difco), 5 g/l yeast extract (Difco), 5 g/l glucose, 5 g/l mannitol, 1 g/l $MgSO_4.7H_2O$, 5 ml/l ethanol, and 15 g/l agar. All other *Acetobacter* strains and all *Gluconobacter* strains were grown at 27° C. for 3 days on mannitol broth (MB) agar medium containing 25 g/l mannitol, 5 g/l yeast extract (Difco Laboratories, Detroit, Mich., USA), 3 g/l Bactopeptone (Difco), and 18 g/l of agar (Difco).

Cells were scraped from the agar plates, suspended in distilled water and used for resting cell reactions conducted at 30° C. for 20 h in 5 ml tubes with shaking at 230 rpm. The reaction mixtures (0.5 ml) contained 1% L-sorbosone, 0.3% NaCl, 1% $CaCO_3$ and cells at a final concentration of 10 absorbance units at 600 nanometers ($OD_{600}$). At the conclusion of the incubation period, the reaction mixtures were analyzed by high performance liquid chromatography (HPLC) using an Agilent 1100 HPLC system (Agilent Technologies, Wilmington, USA) with a LiChrospher-100-RP18 (125×4.6 mm) column (Merck, Darmstadt, Germany) attached to an Aminex-HPX-78H (300×7.8 mm) column (Biorad, Reinach, Switzerland). The mobile phase was 0.004 M sulfuric acid, and the flow rate was 0.6 ml/min. Two signals were recorded using an UV detector (wavelength 254 nm) in combination with a refractive index detector. In addition, the identification of the L-ascorbic acid was done using an amino-column (YMC-Pack Polyamine-II, YMC, Inc., Kyoto, Japan) with UV detection at 254 nm. The mobile phase was 50 mM $NH_4H_2PO_4$ and acetonitrile (40:60).

An Agilent Series 1100 HPLC-mass spectrometry (MS) system was used to identify L-ascorbic acid. The MS was operated in positive ion mode using the electrospray interface. The separation was carried out using a LUNA-C8(2) column (100×4.6 mm) (Phenomenex, Torrance, USA). The mobile phase was a mixture of 0.1% formic acid and methanol (96:4). L-Ascorbic acid eluted with a retention time of 3.1 minutes. The identity of the L-ascorbic acid was confirmed by retention time and the molecular mass of the compound.

To exclude the presence of D-isoascorbic acid, the identification of L-ascorbic acid was additionally done by retention time using an amino-column (YMC-Pack Polyamine-II, YMC, Inc., Kyoto, Japan) with UV detection at 254 nm. The mobile phase was 50 mM $NH_4H_2PO_4$ and acetonitrile (40:60).

The *Gluconobacter* and *Acetobacter* strains produced L-ascorbic acid from L-sorbosone as shown in Table 5.

TABLE 5

Production of L-ascorbic acid from L-sorbosone

| Strain | L-ascorbic acid (mg/L) |
|---|---|
| G. oxydans IFO 3293 | 1740 |
| G. oxydans N44-1 | 570 |
| G. oxydans IFO 3292 | 410 |
| G. oxydans IFO 3244 | 1280 |
| G. frateurii IFO 3260 | 50 |
| G. cerinus IFO 3266 | 140 |
| G. oxydans IFO 3287 | 60 |
| A. aceti subsp. Orleanus IFO 3259 | 30 |
| A. aceti subsp. Xylinum IFO 13693 | 40 |
| A. aceti subsp. Xylinum IFO 13693 | 120 |
| Acetobacter sp. ATCC 15164 | 310 |
| Blank | Not detected |

Blank; reaction was done in the reaction mixture without cells.

EXAMPLE 10

Production of L-Ascorbic Acid from D-Sorbitol, L-Sorbose or L-Sorbosone Using Resting Cells Grown on 3BD Agar Medium Cells of *G. oxydans* N44-1 were grown at 27° C. for 3 days on No. 3BD agar medium containing 70 g/l L-sorbose, 0.5 g/l glycerol, 7.5 g/l yeast extract (Difco), 2.5 g/l $MgSO_4.7H_2O$, 10 g/l $CaCO_3$ and 18 g/l agar (Difco). The resting cell reactions (1 ml reaction mixture in 10 ml tube) were carried out with 2% D-sorbitol, 2% L-sorbose, or 1% L-sorbosone at 30° C. for 24 h as described in Example 9. Strain N44-1 produced 280, 400 and 1780 mg/l of L-ascorbic acid from D-sorbitol, L-sorbose, and L-sorbosone, respectively.

Other reactions (0.5 ml reaction mixture in 10 ml tube) were carried out with N44-1 cells grown on No. 3BD agar medium in reaction mixtures containing 2% D-sorbitol, 2% L-sorbose or 2% L-sorbosone for 2 days as described in Example 9. Strain N44-1 produced 1.8, 2.0 and 5.1 g/l of L-ascorbic acid from D-sorbitol, L-sorbose, and L-sorbosone, respectively.

A reaction using cells of *G. oxydans* IFO 3293 was carried out with 2% L-sorbosone as described above. Strain IFO 3293 produced 5.7 g/l of L-ascorbic acid in 2 days.

EXAMPLE 11

Production of L-Ascorbic Acid from D-Sorbitol Using Resting Cells Grown in Liquid Medium Cells of *G. oxydans* N44-1 were grown in 200 ml of No. 5 medium containing 100 g/l D-sorbitol, 0.5 g/l glycerol, 15 g/l yeast extract (Fluka BioChemika, Buchs, Switzerland), 2.5 g/l $MgSO_4.7H_2O$ and 15 g/l $CaCO_3$ in a 2-1 baffled shake flask at 30° C. with shaking at 180 rpm. After 24 h, the culture was centrifuged at 3220 g (Eppendorf 5810R, Hamburg, Germany), and the cells were resuspended in 0.9% NaCl solution, centrifuged again at 3220 g and the cell pellet was used to inoculate one baffled 500 ml shake flask containing 50 ml of full growth medium (100 g/l D-sorbitol, 0.5 g/l glycerol, 15 g/l yeast extract, 2.5 g/l $MgSO_4.7H_2O$, 15 g/l $CaCO_3$) and another baffled 500 ml shake flask containing 50 ml production medium (100 g/l D-sorbitol, 3 g/l NaCl, 10 g/l $CaCO_3$). The initial cell density, measured as optical density at 600 nm ($OD_{600}$), in both flasks was 10. Both flasks were incubated at 30° C. with shaking at 180 rpm. After 48 h, the cell suspension in growth medium and production medium had accumulated 1.06 and 1.18 g/l L-ascorbic acid, respectively. No additional growth was observed in full medium during the incubation period time.

EXAMPLE 12

Production of L-Ascorbic Acid from L-Sorbosone or D-Sorbitol by Resting Cells of Recombinant Microorganisms with Increased SNDHai Gene Dosage The SNDHai gene of *G. oxydans* N44-1 (SEQ ID NO:1) with upstream and downstream flanking regions was amplified by PCR with chromosomal DNA of strain N44-1 as template and the primer set N1 (SEQ ID NO:28) and N2 (SEQ ID NO:29).

The PCR was done with the GC-rich PCR system (Roche Diagnostics GmbH) according to the instructions of the supplier. The amplified DNA fragment was inserted into vector pCR2.1-TOPO (Invitrogen, Carlsbad, Calif., USA). The resulting plasmid was then digested with HindIII and XhoI. The HindIII-XhoI fragment including the SNDHai gene was ligated to vector pVK100 (available from the American Type Culture Collection, catalog no. ATCC 37156) previously treated with HindIII and XhoI. The ligation mixture was used to transform *E. coli* TG1. The desired plasmid, designated pVK-P-SNDHai-T, was isolated from *E. coli*, and introduced into *G. oxydans* strain N44-1 by electroporation using standard methods (Electrocell manipulator ECM600, BTX Inc., San Diego, Calif., USA).

Three independent transformants, designated N44-1 (pVK-P-SNDHai-T) clone number 1, 2, and 3, together with the parental strain *G. oxydans* N44-1, were each grown on No. 3BD agar and MB agar media. The cells were scraped from the plates and used for resting cell reactions (1% L-sorbosone as the substrate) as described in Example 9. After growth on No. 3BD agar, in the resting cell assay strain N44-1 produced 2.5 g/l L-ascorbic acid, while strains N44-1 (pVK-P-SNDHai-T) clones 1, 2 and 3 produced 4.2, 4.1 and 4.2 g/l L-ascorbic acid, respectively. After growth on MB agar, in the resting cell assay strain N44-1 produced 0.12 g/l L-ascorbic acid, while strains N44-1 (pVK-P-SNDHai-T) clones 1, 2 and 3 produced 1.8, 2.5 and 0.94 g/l L-ascorbic acid, respectively.

Another reaction was carried out using cells of *G. oxydans* N44-1 and clone 2 (see above) cultivated in 50 ml of No. 5 medium (100 g/l D-sorbitol, 0.5 g/l glycerol, 15 g/l yeast extract, 2.5 g/l MgSO$_4$.7H$_2$O, 15 g/l CaCO$_3$) in duplicate 500 ml baffled shake flasks at 30° C. with shaking at 220 rpm for 3 days. From one flask for each strain, the resulting broth was centrifuged at 500 rpm to remove CaCO$_3$. The supernatant from this step was then centrifuged at 5,000 rpm to pellet the cells. The collected cells were re-suspended in 10 ml of 0.9% NaCl solution, and again centrifuged at 5,000 rpm to pellet the cells. The collected cells were re-suspended in water and used to inoculate 1 ml of production medium (20 g/l D-sorbitol, 3 g/l NaCl, 10 g/l CaCO$_3$) in 10 ml reaction tube at a final resting cell density corresponding to 5 OD units at 600 nm. After 20 h reaction time at 30° C. and 220 rpm, the supernatant harvested from the production flask contained 360 and 760 mg/l L-ascorbic acid, respectively for strains N44-1 and N44-1 overexpressing SNDHai. In contrast, after 72 h the supernatant harvested from the remaining growth medium contained 0 and 440 mg/l L-ascorbic acid, respectively.

EXAMPLE 13

Production of L-Ascorbic Acid from L-Sorbosone in Resting Cells of E. coli

The SNDHai gene without stop codon named SNDHai-1, corresponding to nucleotides 1-2364 of SEQ ID NO:1, was amplified from strain N44-1 chromosomal DNA by PCR (Roche High Fidelity kit) using the primer pair SNDHai-Nde (SEQ ID NO:30) and SNDHaiHis-X (SEQ ID NO:31).

The amplified DNA was cloned into pCR2.1-TOPO (Invitrogen, Carlsbad, Calif., USA) to obtain pCR2.1-TOPO-SNDHai-1, whose SNDHai sequence was confirmed to be correct by nucleotide sequencing. Then the SNDHai-1 gene was cut out with NdeI and XhoI and ligated between NdeI and XhoI sites of pET-21b(+) (Novagen, Madison, Wis., USA) to produce pET21b-SNDHaiHis; 6×His was added at the C-terminus of SNDHai. The pET21b-SNDHaiHis was introduced into E. coli BL21 (DE3).

Five ml of one overnight culture of E. coli BL21 (DE3)/pET21b-SNDHaiHis in LB with carbenicillin 50 µg/ml was inoculated into 200 ml of the same medium. The cells were cultivated at 230 rpm at 37° C. for 2 h, then induced with 1 mM IPTG and continued to be cultivated at 230 rpm at 25° C. for 3 h. The resulting culture was centrifuged and washed twice with saline and the cell pellet was resuspended in 2 ml of water. The cells were used for resting cell reaction with the reaction mixture (500 µl in 5 ml tube) containing cells at OD600=10, 1% sorbosone monohydrate, 5 µM PQQ, 5 mM MgCl$_2$, 0.3% NaCl, and 1% CaCO$_3$ conducted at 30° C. for 15 h. 0.14 g/L of L-ascorbic acid was produced after incubation for 15 h. When the resting cell reaction was done with 1 µM PQQ (the other conditions were same as those described above), 0.05 g/L of L-ascorbic acid was produced after incubation for 3 h.

EXAMPLE 14

Production of L-Ascorbic Acid from D-Sorbitol by Resting Cells of Recombinant Microorganisms with Increased SNDHai Gene Dosage Cells of G. oxydans N44-1 overexpressing SNDHai are grown in 50 ml of No. 5 medium containing 100 g/l D-sorbitol, 0.5 g/l glycerol, 15 g/l yeast extract (Fluka BioChemika, Buchs, Switzerland), 2.5 g/l MgSO$_4$.7H$_2$O and 15 g/l CaCO$_3$ in a 500-ml baffled shake flask at 30° C. with shaking at 180 rpm for 48 h. The resulting cell suspension is used to inoculate a 2-L bioreactor, called growth vessel (Biostat-MD, B. Braun Melsungen, Melsungen, Germany) containing 1.25 l of medium composed of 100 g/l D-sorbitol, 15 g/l yeast extract (Fluka BioChemika, Buchs, Switzerland), 2.5 g/l MgSO$_4$.7H$_2$O, 0.3 g/l KH$_2$PO$_4$ and 0.12 g/l CaSO$_4$. Cells are cultivated at 30° C., 1 l/min aeration rate, the pH is controlled to 5.7 with a 25% solution of Na$_2$CO$_3$, dissolved oxygen is controlled to 10% saturation by varying the stirring speed. After 24 h, the cell density measured as absorption units at 600 nm is 20. At this time point, a feed solution containing 100 g/l D-sorbitol, 15 g/l yeast extract (Fluka BioChemika, Buchs, Switzerland), 2.5 g/l MgSO$_4$.7H$_2$O, 0.3 g/l KH$_2$PO$_4$ and 0.12 g/l CaSO$_4$ is fed into the growth vessel at a feed rate of 125 ml/h, and broth is continuously harvested at a harvest rate of 125 ml/h. By this means, the volume in the growth vessel is kept constant at 1.25 l. Other process parameters continue to be controlled as mentioned above.

This broth is continuously fed at a rate of 125 ml/h into a second reactor, called production vessel, filled with 5 l production medium containing 100 g/l D-sorbitol, 0.3 g/l NaCl and 0.12 g/l CaSO$_4$, and the temperature is kept at 30° C., pH at 7.0 by controlling with a 20% solution of NaOH. The aeration rate is kept constant at 10 l/min, and dissolved oxygen is controlled at 20% by varying the stirrer speed. Production medium with the same composition is also continuously fed to the production vessel at a feed rate of 375 ml/h. The vessel volume is kept constant at 5 l by continuously harvesting supernatant at 500 ml/h rate, resulting as a filtrate stream from a crossflow ultrafiltration module with 500 kDa pore size (UFP-500-E-9A, Amersham Biosciences), through which the cell suspension harvested from the production vessel is pumped at 50 l/h using a Masterflex pump. The retentate flow is pumped back into the vessel. Once the cell density in the production vessel reaches 100 absorption units at 600 nm, cells start to be harvested from the concentrated cell stream flowing back into the production vessel at a rate of 25 ml/h, in order to keep the cell density in the production vessel constant.

The harvest stream of cell-free supernatant contains 4 g/l L-ascorbic acid and is continuously fed at a rate of 500 ml/h into a collecting vessel with a double jacket at 30° C. (Ecoline Re112, Lauda, Lauda-Koenigshofen, Germany). This vessel feeds continuously supernatant to the diluate compartment of a two-compartment electrodialysis unit (stack containing 10 cell pairs with cation exchange membranes CMX-S and anion exchange membranes ASM, total membrane area 0.2 m$^2$, from Eurodia Industries, Wissous, France) at a rate of 180 l/h, and a constant stream is pumped out of the vessel to keep its volume constant at 2 l. Another vessel with double jacket containing initially deionized water at 30° C. is continuously fed with fresh deionized water at a rate of 62.5 ml/h, pumps constantly aqueous solution into the concentrate compartment of the electrodialysis unit at a rate of 200 l/h, and a constant harvest stream is pumped out of the vessel. Feed solutions are pumped to the electrodialysis stack using peristaltic pumps (7518-00, Masterflex, USA), and recirculation of solutions through each electrodialysis compartment is done with help of rotary pumps (MD-20, IWAK, Tokyo, Japan). During the whole process, 14 V are applied to the electrodialysis stack (power source FuMATech TS001/5, St. Ingbert, Germany). The concentration of L-ascorbic acid in the harvest stream is 16 g/l.

EXAMPLE 15

Purification of L-Ascorbic Acid Produced by a Resting Cell Reaction Via Downstream Processing Steps The harvest stream of Example 14 containing 16 g/l L-ascorbic acid is fed to a chelating resin (Amberlite IRC 748, Rohm and Haas, Philadelphia, Pa., USA) to eliminate divalent cations from the stream. It is then collected in a cooled vessel (feed vessel), and when 10 l have been collected, they are processed in batch mode through a bipolar membrane electrodialysis unit (stack containing 7 Neosepta BP1/CMB membranes, total membrane area 0.14 m$^2$, from Eurodia Industries, Wissous, France). This solution is pumped at 200 l/h through the feed compartment of the electrodialysis unit, and recycled into the feed vessel. Another cooled vessel (concentrate vessel) containing initially 5 l of a 2 g/l NaOH solution is pumped at 100 l/h through the concentrate compartment of the bipolar membrane electrodialysis unit. By applying a maximal voltage of 25 V and maximal electric current of 20 A, sodium cations from the feed compartment are transferred to the concentrate compartment, and thus the sodium form of L-ascorbic acid present in the feed stream is converted into the corresponding free acid form. After reaching 90% conversion yield, the process is stopped. In the concentrate vessel, 6 l of solution containing 7.5 g/l NaOH are collected in the diluate vessel, 9 l solution containing about 16 g/l L-ascorbic acid in its free acid form and 1.6 g/l L-ascorbic acid in its sodium salt form are further processed through a cation exchange resin (Amberlite FPC 21H, Rohm and Haas, Philadelphia, Pa., USA), in order to increase conversion yield of the sodium salt into the free acid form to about 99%. Alternatively, the 10 l solution containing 16 g/l L-ascorbic acid in its sodium salt form coming from the electrodialysis step is directly treated by cation exchange resin, being converted to the free acid form at 99% yield. The stream of L-ascorbic acid in the form of the free acid, obtained by either of the methods described above, is then further processed by a sequence of the following steps: anion exchange, activated carbon treatment, concentration, crystallization, filtration of the crystals, and drying. The final purity of the obtained crystals is 98%, and the yield obtained with the combined downstream processing steps is 80%.

The invention claimed is:

1. An isolated polypeptide comprising the amino acid sequence of SEQ ID NO:16, wherein the polypeptide has L-sorbosone dehydrogenase activity.

2. The isolated polypeptide of claim 1, wherein the polypeptide consists of SEQ ID NO: 16, and has L-sorbosone dehydrogenase activity.

3. An isolated polypeptide comprising the amino acid sequence of SEQ ID NO:2, wherein the polypeptide has L-sorbosone dehydrogenase activity.

4. An isolated polypeptide consisting of the amino acid sequence of SEQ ID NO:2, wherein the polypeptide has L-sorbosone dehydrogenase activity.

* * * * *

UNITED STATES PATENT AND TRADEMARK OFFICE
CERTIFICATE OF CORRECTION

| | | |
|---|---|---|
| PATENT NO. | : 7,700,723 B2 | Page 1 of 1 |
| APPLICATION NO. | : 10/567763 | |
| DATED | : April 20, 2010 | |
| INVENTOR(S) | : Alan Berry et al. | |

It is certified that error appears in the above-identified patent and that said Letters Patent is hereby corrected as shown below:

In column 64, line 13, cancel the text beginning with, "4. An isolated polypeptide" to and ending, "L-sorbosone dehydrogenase activity." in col. 4, line 15, and insert the following claim:

-- 4. The isolated polypeptide of claim 3, wherein the polypeptide consists of SEQ ID NO. 2, and has L-curbstone dehydrogenase activity. --

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,700,723 B2  Page 1 of 1
APPLICATION NO. : 10/567763
DATED : April 20, 2010
INVENTOR(S) : Alan Berry et al.

It is certified that error appears in the above-identified patent and that said Letters Patent is hereby corrected as shown below:

In column 64, line 13, cancel the text beginning with, "4. An isolated polypeptide" to and ending, "L-sorbosone dehydrogenase activity." in col. 4, line 15, and insert the following claim:

-- 4. The isolated polypeptide of claim 3, wherein the polypeptide consists of SEQ ID NO. 2, and has L-sorbosone dehydrogenase activity. --

This certificate supersedes the Certificate of Correction issued June 1, 2010.

Signed and Sealed this

Thirteenth Day of July, 2010

David J. Kappos
*Director of the United States Patent and Trademark Office*

```
                        SEQUENCE LISTING

<160> NUMBER OF SEQ ID NOS: 31

<210> SEQ ID NO 1
<211> LENGTH: 2367
<212> TYPE: DNA
<213> ORGANISM: Gluconobacter oxydans N44-1

<400> SEQUENCE: 1
atgaacagcg gcccccgcac gctctccatg atcatcggga ttctgggcgc cctcatggcc      60
gccttcctga tcatcgaagg cctccacctc atcatcctcg gcggctcgtg gttctacacc     120
ctcgccggca tcgcgctggc ggccagcagc gtctacatga tccgtcgcaa catcctctcg     180
acatggatcg ccctgggcct gcttgtggca acagccctgt ggtcgctcgc cgaagtcggc     240
accagcttct ggcccagctt ctcccgcctg atcgtgttcc tgtgcgtcgc cctgatcgcg     300
actctcatgg cgccctggct cagcggcccc ggccggcgct acttcacccg ccccgtcaca     360
ggcgccacat ccggcgccct cggcgcgatc atcgtggctt tcctcgccgg catgttccgg     420
gtccacccga ccatcgcccc gcaggacacc acccacccgc aggaaaccgc gtccaccgcc     480
gactccgacc agccaggcca tgactggccc gcctatggcc gcacggcttc cggcacgcgc     540
tacgccagct tcacgcagat caaccgcgac aatgtcagca gctccgcgt cgcctggacc     600 taccgcaccg gcgacatggc gctgaacggc gccgagttcc agggcacccc catcaagatc     660
ggcgacacgg tctatatctg ctcaccgcac aacatcgtct cggcccttga cccggacacc     720
ggcacggaaa agtggaagtt cgaccccac gcccagacga aagtctggca gcgctgccgc     780
ggcgtcggct actggcatga cagcacggcc acggacgcca acgcgccctg cgcctcgcgc     840
atcgtcctca ccacgatcga cgcccgcctc atcaccatcg acgcccgtac cggccaggcc     900
tgcacggatt tcggaacgaa cggcaacgtc aatctcctga ccggcctcgg cccgacagct     960
cccggctcgt actacccgac cgccgcccc ctcgtggcgg gtgacatcgt ggtcgtcggc    1020
ggccgcatcg ccgataacga gcgcaccggc gagccctccg gcgtcgtccg cggctatgat    1080
gtccgcaccg gcgcacaggt ctgggcctgg gacgccacca acccgcatcg cggcaccaca    1140
```

```
cctctggccg aaggcgagat ctaccccgcc gaaaccccca acatgtgggg caccgccagc    1200
tacgacccga aactcaacct cgtcttcttc ccgctcggca accagacccc cgatttctgg    1260
ggcggcgacc gcagcaaggc ctcagacgaa tacaacgacg ccttcgtcgc cgtggacgcc    1320
aagaccggcg acgaacgctg gcacttccgc accgccaacc acgacctcgt ggactacgat    1380
gccacgcccc agcccatcct ctatgacatt ccggacggcc atggcggcac ccgcccggcg    1440
atcatcgcca tgaccaagcg cggccagatc ttcgtgctcg accgccgcga cggcaccccg    1500
atcgtccctg tggaaatgcg caaagtcccg caggacggcg caccggaaca ccagtacctc    1560
gcccccgaac agccctattc cgccctctcc atcggaacag agcgcctgaa acccagcgac    1620
atgtggggtg gtacgatctt cgaccagctc ctgtgccgca tccagttcgc ctcctaccgc    1680
tatgaaggcg agttcacccc cgtcaacgag aaacaggcca ccatcatcta ccgggctat     1740 tacggcggca tcaactgggg cggcggcgcc gtggatgaaa gcaccggaac gctgctggtc    1800
aacgacatcc gcatggccca gtggggcaag ttcatgaagc aggaagaagc ccgtcgcagc    1860
ggcttcaaac ccagctcgga aggcgaatat ccgaacagaa aaggcacccc ctggggcgtc    1920
gtccgctcga tgttcttctc ccccgccggt ctccccctgcg tgaaaccgcc ctatggcacg    1980
atgaacgcca tcgacctgcg cagcggcaag gtcaaatgga gcatgccgct ggcacgatc    2040 caggacatgc cggtccacgg catggtccca ggcctcgcca tccgctcgg aatgccgacc     2100 atgagcggcc cgctggccac ccataccggc ctggtgttct ctccggcac gctcgacaac     2160 tatgtccgcg cgctcaacac cgacaccggc gaagtcgtct ggaaagcccg tctccccgtc    2220
gcctcacagg ccgctccgat gagctacatg tccgacaaga ccggcaaaca gtacatcgtc    2280
gtcaccgcag gcggcctgac ccgctccggc gtcgacaaaa accgcggcga ctacgtcatc    2340
gcctacgccc tgccctccga agaataa                                         2367

<210> SEQ ID NO 2
<211> LENGTH: 788
<212> TYPE: PRT
<213> ORGANISM: Gluconobacter oxydans N44-1

<400> SEQUENCE: 2

Met Asn Ser Gly Pro Arg Thr Leu Ser Met Ile Ile Gly Ile Leu Gly
1               5                   10                  15

Ala Leu Met Ala Ala Phe Leu Ile Ile Glu Gly Leu His Leu Ile Ile
                20                  25                  30

Leu Gly Gly Ser Trp Phe Tyr Thr Leu Ala Gly Ile Ala Leu Ala Ala
            35                  40                  45

Ser Ser Val Tyr Met Ile Arg Arg Asn Ile Leu Ser Thr Trp Ile Ala
        50                  55                  60

Leu Gly Leu Leu Val Ala Thr Ala Leu Trp Ser Leu Ala Glu Val Gly
65                  70                  75                  80

Thr Ser Phe Trp Pro Ser Phe Ser Arg Leu Ile Val Phe Leu Cys Val
                85                  90                  95

Ala Leu Ile Ala Thr Leu Met Ala Pro Trp Leu Ser Gly Pro Gly Arg
                100                 105                 110

Arg Tyr Phe Thr Arg Pro Val Thr Gly Ala Thr Ser Gly Ala Leu Gly
            115                 120                 125

Ala Ile Ile Val Ala Phe Leu Ala Gly Met Phe Arg Val His Pro Thr
        130                 135                 140

Ile Ala Pro Gln Asp Thr Thr His Pro Gln Glu Thr Ala Ser Thr Ala
145                 150                 155                 160
```

-continued

```
Asp Ser Asp Gln Pro Gly His Asp Trp Pro Ala Tyr Gly Arg Thr Ala
            165                 170                 175
Ser Gly Thr Arg Tyr Ala Ser Phe Thr Gln Ile Asn Arg Asp Asn Val
        180                 185                 190
Ser Lys Leu Arg Val Ala Trp Thr Tyr Arg Thr Gly Asp Met Ala Leu
    195                 200                 205
Asn Gly Ala Glu Phe Gln Gly Thr Pro Ile Lys Ile Gly Asp Thr Val
210                 215                 220
Tyr Ile Cys Ser Pro His Asn Ile Val Ser Ala Leu Asp Pro Asp Thr
225                 230                 235                 240
Gly Thr Glu Lys Trp Lys Phe Asp Pro His Ala Gln Thr Lys Val Trp
                245                 250                 255
Gln Arg Cys Arg Gly Val Gly Tyr Trp His Asp Ser Thr Ala Thr Asp
            260                 265                 270
Ala Asn Ala Pro Cys Ala Ser Arg Ile Val Leu Thr Thr Ile Asp Ala
        275                 280                 285
Arg Leu Ile Thr Ile Asp Ala Arg Thr Gly Gln Ala Cys Thr Asp Phe
    290                 295                 300
Gly Thr Asn Gly Asn Val Asn Leu Leu Thr Gly Leu Gly Pro Thr Ala
305                 310                 315                 320
Pro Gly Ser Tyr Tyr Pro Thr Ala Ala Pro Leu Val Ala Gly Asp Ile
                325                 330                 335
Val Val Val Gly Gly Arg Ile Ala Asp Asn Glu Arg Thr Gly Glu Pro
            340                 345                 350
Ser Gly Val Val Arg Gly Tyr Asp Val Arg Thr Gly Ala Gln Val Trp
        355                 360                 365
Ala Trp Asp Ala Thr Asn Pro His Arg Gly Thr Thr Pro Leu Ala Glu
    370                 375                 380
Gly Glu Ile Tyr Pro Ala Glu Thr Pro Asn Met Trp Gly Thr Ala Ser
385                 390                 395                 400
Tyr Asp Pro Lys Leu Asn Leu Val Phe Phe Pro Leu Gly Asn Gln Thr
                405                 410                 415
Pro Asp Phe Trp Gly Gly Asp Arg Ser Lys Ala Ser Asp Glu Tyr Asn
            420                 425                 430
Asp Ala Phe Val Ala Val Asp Ala Lys Thr Gly Asp Glu Arg Trp His
        435                 440                 445
Phe Arg Thr Ala Asn His Asp Leu Val Asp Tyr Asp Ala Thr Ala Gln
    450                 455                 460
Pro Ile Leu Tyr Asp Ile Pro Asp Gly His Gly Gly Thr Arg Pro Ala
465                 470                 475                 480
Ile Ile Ala Met Thr Lys Arg Gly Gln Ile Phe Val Leu Asp Arg Arg
                485                 490                 495
Asp Gly Thr Pro Ile Val Pro Val Glu Met Arg Lys Val Pro Gln Asp
            500                 505                 510
Gly Ala Pro Glu His Gln Tyr Leu Ala Pro Glu Gln Pro Tyr Ser Ala
        515                 520                 525
Leu Ser Ile Gly Thr Glu Arg Leu Lys Pro Ser Asp Met Trp Gly Gly
    530                 535                 540
Thr Ile Phe Asp Gln Leu Leu Cys Arg Ile Gln Phe Ala Ser Tyr Arg
545                 550                 555                 560
Tyr Glu Gly Glu Phe Thr Pro Val Asn Glu Lys Gln Ala Thr Ile Ile
                565                 570                 575
```

-continued

Tyr Pro Gly Tyr Tyr Gly Gly Ile Asn Trp Gly Gly Ala Val Asp
             580                 585                 590

Glu Ser Thr Gly Thr Leu Leu Val Asn Asp Ile Arg Met Ala Gln Trp
             595                 600                 605

Gly Lys Phe Met Lys Gln Glu Glu Ala Arg Arg Ser Gly Phe Lys Pro
        610                 615                 620

Ser Ser Glu Gly Glu Tyr Ser Glu Gln Lys Gly Thr Pro Trp Gly Val
625                 630                 635                 640

Val Arg Ser Met Phe Phe Ser Pro Ala Gly Leu Pro Cys Val Lys Pro
                645                 650                 655

Pro Tyr Gly Thr Met Asn Ala Ile Asp Leu Arg Ser Gly Lys Val Lys
            660                 665                 670

Trp Ser Met Pro Leu Gly Thr Ile Gln Asp Met Pro Val His Gly Met
            675                 680                 685

Val Pro Gly Leu Ala Ile Pro Leu Gly Met Pro Thr Met Ser Gly Pro
            690                 695                 700

Leu Ala Thr His Thr Gly Leu Val Phe Phe Ser Gly Thr Leu Asp Asn
705                 710                 715                 720

Tyr Val Arg Ala Leu Asn Thr Asp Thr Gly Glu Val Val Trp Lys Ala
                725                 730                 735

Arg Leu Pro Val Ala Ser Gln Ala Ala Pro Met Ser Tyr Met Ser Asp
                740                 745                 750

Lys Thr Gly Lys Gln Tyr Ile Val Val Thr Ala Gly Gly Leu Thr Arg
            755                 760                 765

Ser Gly Val Asp Lys Asn Arg Gly Asp Tyr Val Ile Ala Tyr Ala Leu
            770                 775                 780

Pro Ser Glu Glu
785

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
cgccttctat gaaaggttgg                                          20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
agcggatgga gatcgggcgg                                          20

<210> SEQ ID NO 5
<211> LENGTH: 30
<212> TYPE: DNA
<213> ORGANISM: Artificial
<220> FEATURE:
<223> OTHER INFORMATION: Primer

<400> SEQUENCE: 5
atgaacagcg gcccccgcac gctctccatg                               30

```
<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
ccggaacatg ccggcgagga aagccacgat                                      30

<210> SEQ ID NO 7
<211> LENGTH: 30
<212> TYPE: DNA
<213> ORGANISM: Artificial
<220> FEATURE:
<223> OTHER INFORMATION: Primer

<400> SEQUENCE: 7
tgactggccc gcctatggcc gcacggcttc                                      30

<210> SEQ ID NO 8
<211> LENGTH: 30
<212> TYPE: DNA
<213> ORGANISM: Artificial
<220> FEATURE:
<223> OTHER INFORMATION: Primer

<400> SEQUENCE: 8
ttcttcggag ggcagggcgt aggcgatgac                                      30

<210> SEQ ID NO 9
<211> LENGTH: 30
<212> TYPE: DNA
<213> ORGANISM: Artificial
<220> FEATURE:
<223> OTHER INFORMATION: Primer

<400> SEQUENCE: 9
cgggactttg cgcatttcca cagggacgat                                      30

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
agcccatcct ctatgacatt ccggacggcc                                      30

<210> SEQ ID NO 11
<211> LENGTH: 771
<212> TYPE: DNA
<213> ORGANISM: Gluconobacter oxydans IFO 3292

<400> SEQUENCE: 11
ccgcccggcg atcatcgcca tgaccaagcg cggccagatc ttcgtgctcg accgccgcga      60
cggcaccccg atcgtccccg tggaaatgcg caaagtcccc caggacggcg caccggaaca    120
ccagtacctc gccccgaac agccctattc cgccctctcc atcggaacag agcgcctgaa    180
acccagcgat atgtggggcg gcacgatctt cgaccagctc ctgtgccgca tccagttcgc    240
ctcctaccgc tatgaaggcg agttcacccc cgtcaacgag aagcaggcca ccatcatcta    300
tccgggctat tacggcggca tcaactgggg cggcggcgcc gtggatgaaa gcaccggaac    360
```

-continued

```
gctgctggtc aacgacatcc gcatggccca gtggggcaag ttcatgaagc aagaagaagc    420
ccgccgcagc ggcttcaaac ccagctcgga aggcgaatat ccgaacaga aaggcacccc    480 ctggggcgtc gtccgctcga tgttcttctc ccccgccggt ctcccctgcg tgaaaccgcc    540
ctatggcacg atgaacgcca tcgacctgcg cagcggcaag gtcaaatgga gcatgccgct    600
tggcacgatc caggacatgc cggtccacgg catggtcccc ggcctcgcca tcccgctcgg    660
aatgccgacc atgagcggcc cgctggccac ccataccggc ctggtcttct tctccggcac    720
gctcgacaac tatgtccgcg cgctcaacac cgacaccggc gaagtcgtct g             771
```

<210> SEQ ID NO 12
<211> LENGTH: 256
<212> TYPE: PRT
<213> ORGANISM: Gluconobacter oxydans IFO 3292

<400> SEQUENCE: 12

Arg Pro Ala Ile Ile Ala Met Thr Lys Arg Gly Gln Ile Phe Val Leu
1               5                   10                  15

Asp Arg Arg Asp Gly Thr Pro Ile Val Pro Val Glu Met Arg Lys Val
            20                  25                  30

Pro Gln Asp Gly Ala Pro Glu His Gln Tyr Leu Ala Pro Glu Gln Pro
        35                  40                  45

Tyr Ser Ala Leu Ser Ile Gly Thr Glu Arg Leu Lys Pro Ser Asp Met
    50                  55                  60

Trp Gly Gly Thr Ile Phe Asp Gln Leu Leu Cys Arg Ile Gln Phe Ala
65                  70                  75                  80

Ser Tyr Arg Tyr Glu Gly Glu Phe Thr Pro Val Asn Glu Lys Gln Ala
                85                  90                  95

Thr Ile Ile Tyr Pro Gly Tyr Tyr Gly Ile Asn Trp Gly Gly Gly
            100                 105                 110

Ala Val Asp Glu Ser Thr Gly Thr Leu Leu Val Asn Asp Ile Arg Met
        115                 120                 125

Ala Gln Trp Gly Lys Phe Met Lys Gln Glu Glu Ala Arg Arg Ser Gly
    130                 135                 140

Phe Lys Pro Ser Ser Glu Gly Glu Tyr Ser Glu Gln Lys Gly Thr Pro
145                 150                 155                 160

Trp Gly Val Val Arg Ser Met Phe Phe Ser Pro Ala Gly Leu Pro Cys
                165                 170                 175

Val Lys Pro Pro Tyr Gly Thr Met Asn Ala Ile Asp Leu Arg Ser Gly
            180                 185                 190

Lys Val Lys Trp Ser Met Pro Leu Gly Thr Ile Gln Asp Met Pro Val
        195                 200                 205

His Gly Met Val Pro Gly Leu Ala Ile Pro Leu Gly Met Pro Thr Met
    210                 215                 220

Ser Gly Pro Leu Ala Thr His Thr Gly Leu Val Phe Phe Ser Gly Thr
225                 230                 235                 240

Leu Asp Asn Tyr Val Arg Ala Leu Asn Thr Asp Thr Gly Glu Val Val
                245                 250                 255

<210> SEQ ID NO 13
<211> LENGTH: 350
<212> TYPE: DNA
<213> ORGANISM: Gluconobacter oxydans IFO 3287
<220> FEATURE:
<221> NAME/KEY: misc_feature
<222> LOCATION: (123)..(123)
<223> OTHER INFORMATION: n is a or c or g or t

<400> SEQUENCE: 13

```
atcatcggga ttctgggcgc cctcatggcc gccttcctga tcatcgaagg cctccacctc     60
atcatcctcg gcggctcatg gttttacacc ctcgccggca tcgcgctggc agccagcagc    120
gtntacatga tccgtcgcaa catcctctcg acatggatcg ccctcggcct gcttgtggca    180
acagccctgt ggtcgctcgc cgaagtcggc accagcttct ggcccagctt ctcccgcctg    240
atcgtatttc tgtgcgtcgc cctgatcgcg accctcatgg cgccctggct cagcggcccc    300
ggccggcgct acttcacccg ccccgtcaca ggcgccacct ccggcgccct                350
```

<210> SEQ ID NO 14
<211> LENGTH: 116
<212> TYPE: PRT
<213> ORGANISM: Gluconobacter oxydans IFO 3287

<400> SEQUENCE: 14

```
Ile Ile Gly Ile Leu Gly Ala Leu Met Ala Ala Phe Leu Ile Ile Glu
 1               5                  10                  15

Gly Leu His Leu Ile Ile Leu Gly Gly Ser Trp Phe Tyr Thr Leu Ala
            20                  25                  30

Gly Ile Ala Leu Ala Ala Ser Ser Val Tyr Met Ile Arg Arg Asn Ile
        35                  40                  45

Leu Ser Thr Trp Ile Ala Leu Gly Leu Leu Val Ala Thr Ala Leu Trp
    50                  55                  60

Ser Leu Ala Glu Val Gly Thr Ser Phe Trp Pro Ser Phe Ser Arg Leu
65                  70                  75                  80

Ile Val Phe Leu Cys Val Ala Leu Ile Ala Thr Leu Met Ala Pro Trp
                85                  90                  95

Leu Ser Gly Pro Gly Arg Arg Tyr Phe Thr Arg Pro Val Thr Gly Ala
            100                 105                 110

Thr Ser Gly Ala
        115
```

<210> SEQ ID NO 15
<211> LENGTH: 808
<212> TYPE: DNA
<213> ORGANISM: Gluconobacter oxydans IFO 3287

<400> SEQUENCE: 15

```
gcaagctccg cgtcgcctgg acctaccgca ctggcgacat ggcgctgaac ggggccgagt     60
tccagggcac ccccatcaag atcggcgaca cggtctatat ctgctcgccg cacaacatcg    120
tctcggccct cgaccccgat accggcacgg aaaagtggaa gttcgacccc cacgcccaga    180
cgaaagtctg gcagcgctgc cgcggcgtcg gctactggca tgacagcacg gccacggacg    240
ccaacgcgcc ctgcgcctcg cgcatcgtcc tcaccacgat cgacgcccgc ctcatcacca    300
tcgacgcccg caccggccag gcctgcacgg atttcggaac gaacggcaac gtcaatctcc    360
tgaccggcct cggcccgaca gccccggtt cctactaccc gaccgccgcc ccctcgtgg    420
ccggtgacat cgtggtcgtc ggcggccgca tcgccgataa cgagcgcacc ggcgaaccct    480
ccggcgtcgt ccgcggctat gacgtccgca ccggcgcgca ggtctgggcc tgggacgcca    540
ccaacccgca tcgcggcacc acaccgctgg ccgaaggcga gatctatccc gccgaaaccc    600
ccaacatgtg gggcaccgcc agctacgacc cgaagctcaa cctcgtcttc ttcccgctcg    660
gcaaccagac ccccgatttc tggggcggcg accgcagcaa ggcttctgat gaatacaacg    720
```

```
acgccttcgt cgccgtggac gccaagaccg gcgacgaacg ctggcacttc cgcaccgcca    780
accacgacct cgtggactac gatgccac                                       808

<210> SEQ ID NO 16
<211> LENGTH: 268
<212> TYPE: PRT
<213> ORGANISM: Gluconobacter oxydans IFO 3287

<400> SEQUENCE: 16

Lys Leu Arg Val Ala Trp Thr Tyr Arg Thr Gly Asp Met Ala Leu Asn
1               5                   10                  15

Gly Ala Glu Phe Gln Gly Thr Pro Ile Lys Ile Gly Asp Thr Val Tyr
            20                  25                  30

Ile Cys Ser Pro His Asn Ile Val Ser Ala Leu Asp Pro Asp Thr Gly
        35                  40                  45

Thr Glu Lys Trp Lys Phe Asp Pro His Ala Gln Thr Lys Val Trp Gln
    50                  55                  60

Arg Cys Arg Gly Val Gly Tyr Trp His Asp Ser Thr Ala Thr Asp Ala
65                  70                  75                  80

Asn Ala Pro Cys Ala Ser Arg Ile Val Leu Thr Thr Ile Asp Ala Arg
                85                  90                  95

Leu Ile Thr Ile Asp Ala Arg Thr Gly Gln Ala Cys Thr Asp Phe Gly
            100                 105                 110

Thr Asn Gly Asn Val Asn Leu Leu Thr Gly Leu Gly Pro Thr Ala Pro
        115                 120                 125

Gly Ser Tyr Tyr Pro Thr Ala Ala Pro Leu Val Ala Gly Asp Ile Val
    130                 135                 140

Val Val Gly Gly Arg Ile Ala Asp Asn Glu Arg Thr Gly Glu Pro Ser
145                 150                 155                 160

Gly Val Val Arg Gly Tyr Asp Val Arg Thr Gly Ala Gln Val Trp Ala
                165                 170                 175

Trp Asp Ala Thr Asn Pro His Arg Gly Thr Thr Pro Leu Ala Glu Gly
            180                 185                 190

Glu Ile Tyr Pro Ala Glu Thr Pro Asn Met Trp Gly Thr Ala Ser Tyr
        195                 200                 205

Asp Pro Lys Leu Asn Leu Val Phe Phe Pro Leu Gly Asn Gln Thr Pro
    210                 215                 220

Asp Phe Trp Gly Gly Asp Arg Ser Lys Ala Ser Asp Glu Tyr Asn Asp
225                 230                 235                 240

Ala Phe Val Ala Val Asp Ala Lys Thr Gly Asp Glu Arg Trp His Phe
                245                 250                 255

Arg Thr Ala Asn His Asp Leu Val Asp Tyr Asp Ala
            260                 265

<210> SEQ ID NO 17
<211> LENGTH: 800
<212> TYPE: DNA
<213> ORGANISM: Gluconobacter oxydans IFO 3287

<400> SEQUENCE: 17
tcttcgtgct cgaccgccgc gacggcaccc cgatcgtccc cgtggaaatg cgcaaagtcc    60
cgcaggacgg cgcaccggaa caccagtacc tcgcccccga acagccctat tccgccctct   120
ccatcggaac agagcgcctg aaacccagcg atatgtgggg tggtacgatt ttcgaccagc   180
tcctgtgccg catccagttc gcctcctacc gctatgaagg cgagttcacc cccgtcaacg   240
```

```
agaaacaggc caccatcatc tatccgggct attacggcgg catcaactgg ggcggcggcg    300
ccgtggatga aagcaccgga acgctgctgg tcaacgacat ccgcatggcc cagtggggca    360
agttcatgaa gcaggaagaa gcccgtcgca gcggcttcaa acccagctcg aaggcgaat    420
attccgaaca gaaaggcacc ccctgggggcg tcgtccgctc gatgttcttc tccccgccg    480
gtctcccctg cgtaaaaccg ccctatggca cgatgaacgc catcgacctg cgcagcggca    540
aggtgaaatg gagcatgccg cttggcacga tccaggacat gccggtccac ggcatggtcc    600
caggcctcgc catcccgctc ggaatgccaa ccatgagcgg cccgctggcc acccataccg    660
gcttggtctt cttctccggc acgctcgaca actacgtccg cgcgctcaac accgacaccg    720
gcgaggtcgt ctggaaagcc cgtctccccg tcgcctcaca ggccgctccg atgagctaca    780
tgtccgacaa gaccggcaaa                                                 800
```

<210> SEQ ID NO 18
<211> LENGTH: 266
<212> TYPE: PRT
<213> ORGANISM: Gluconobacter oxydans IFO 3287

<400> SEQUENCE: 18

```
Phe Val Leu Asp Arg Arg Asp Gly Thr Pro Ile Val Pro Val Glu Met
 1               5                  10                  15

Arg Lys Val Pro Gln Asp Gly Ala Pro Glu His Gln Tyr Leu Ala Pro
            20                  25                  30

Glu Gln Pro Tyr Ser Ala Leu Ser Ile Gly Thr Glu Arg Leu Lys Pro
        35                  40                  45

Ser Asp Met Trp Gly Gly Thr Ile Phe Asp Gln Leu Leu Cys Arg Ile
    50                  55                  60

Gln Phe Ala Ser Tyr Arg Tyr Glu Gly Glu Phe Thr Pro Val Asn Glu
65                  70                  75                  80

Lys Gln Ala Thr Ile Ile Tyr Pro Gly Tyr Tyr Gly Ile Asn Trp
            85                  90                  95

Gly Gly Gly Ala Val Asp Glu Ser Thr Gly Thr Leu Leu Val Asn Asp
           100                 105                 110

Ile Arg Met Ala Gln Trp Gly Lys Phe Met Lys Gln Glu Glu Ala Arg
       115                  120                 125

Arg Ser Gly Phe Lys Pro Ser Glu Gly Glu Tyr Ser Glu Gln Lys
           130                 135                 140

Gly Thr Pro Trp Gly Val Val Arg Ser Met Phe Phe Ser Pro Ala Gly
145                 150                 155                 160

Leu Pro Cys Val Lys Pro Pro Tyr Gly Thr Met Asn Ala Ile Asp Leu
               165                 170                 175

Arg Ser Gly Lys Val Lys Trp Ser Met Pro Leu Gly Thr Ile Gln Asp
           180                 185                 190

Met Pro Val His Gly Met Val Pro Gly Leu Ala Ile Pro Leu Gly Met
           195                 200                 205

Pro Thr Met Ser Gly Pro Leu Ala Thr His Thr Gly Leu Val Phe Phe
       210                 215                 220

Ser Gly Thr Leu Asp Asn Tyr Val Arg Ala Leu Asn Thr Asp Thr Gly
225                 230                 235                 240

Glu Val Val Trp Lys Ala Arg Leu Pro Val Ala Ser Gln Ala Ala Pro
               245                 250                 255

Met Ser Tyr Met Ser Asp Lys Thr Gly Lys
           260                 265
```

<210> SEQ ID NO 19
<211> LENGTH: 360
<212> TYPE: DNA
<213> ORGANISM: Acetobacter sp. ATCC 15164
<220> FEATURE:
<221> NAME/KEY: misc_feature
<222> LOCATION: (123)..(123)
<223> OTHER INFORMATION: n is a or c or g or t

<400> SEQUENCE: 19

```
atcatcggga ttctgggcgc cctcatggcc gccttcctga tcatcgaagg cctccacctc    60
atcatcctcg gcggctcgtg gttttacacc ctcgccggca tcgcgctggc ggccagcagc   120
gtntacatga tccgtcgcaa catcctctcg acatggatcg ccctcggcct gcttgtagca   180
acagccctgt ggtcgctcgc cgaagtcggc accagcttct ggcccagctt ctcccgcctg   240
atcgtgttcc tgtgcgtcgc cctgatcgcg actctcatgg cgccctggct cagcggcccc   300
ggccggcgct acttcacccg ccccgtcaca ggggccacct ccggcgcact cggcgccatc   360
```

<210> SEQ ID NO 20
<211> LENGTH: 120
<212> TYPE: PRT
<213> ORGANISM: Acetobacter sp. ATCC 15164

<400> SEQUENCE: 20

```
Ile Ile Gly Ile Leu Gly Ala Leu Met Ala Ala Phe Leu Ile Ile Glu
1               5                   10                  15
Gly Leu His Leu Ile Ile Leu Gly Gly Ser Trp Phe Tyr Thr Leu Ala
            20                  25                  30
Gly Ile Ala Leu Ala Ala Ser Ser Val Tyr Met Ile Arg Arg Asn Ile
        35                  40                  45
Leu Ser Thr Trp Ile Ala Leu Gly Leu Leu Val Ala Thr Ala Leu Trp
    50                  55                  60
Ser Leu Ala Glu Val Gly Thr Ser Phe Trp Pro Ser Phe Ser Arg Leu
65                  70                  75                  80
Ile Val Phe Leu Cys Val Ala Leu Ile Ala Thr Leu Met Ala Pro Trp
                85                  90                  95
Leu Ser Gly Pro Gly Arg Arg Tyr Phe Thr Arg Pro Val Thr Gly Ala
            100                 105                 110
Thr Ser Gly Ala Leu Gly Ala Ile
        115                 120
```

<210> SEQ ID NO 21
<211> LENGTH: 760
<212> TYPE: DNA
<213> ORGANISM: Acetobacter sp. ATCC 15164

<400> SEQUENCE: 21

```
accgcgacaa tgtcagcaag ctccgcgtcg cctggaccta ccgcaccggc gacatggcgc    60
tgaacggcgc cgaattccag ggcaccccca tcaagatcgg cgatacggtc tatatctgct   120
caccccacaa catcgtctcg gccctcgacc ccgacaccgg cacggaaaag tggaagttcg   180
acccccacgc ccagacgaaa gtctggcagc gctgccgcgg cgtcggctac tggcatgaca   240
gcacagccac ggacgccaac gcgccctgcg cctcgcgcat cgtcctcacc acgatcgacg   300
cccgcctcat caccatcgac gccgcaccg gccaggcctg cacggatttc ggaacgaacg   360
gcaacgtcaa tctcctgacc ggcctcggcc cgacagcccc cggctcctac tacccgaccg   420
ccgcccccct cgtggcgggt gacatcgtgg tcgtcggcgg ccgcatcgcc gataacgagc   480
```

```
gcacaggcga gccttccggc gtcgtccgcg gctacgacgt ccgcaccggc gcacaggtct    540
gggcctggga cgccaccaac ccgcatcgcg gcaccacacc actggccgaa ggcgagatct    600
accccgccga aaccccaac atgtggggca ccgccagcta cgacccgaaa ctcaacctcg    660
tcttcttccc gctcggcaac cagaccccccg atttctgggg cggcgaccgc agcaaggcct    720
cggatgaata caacgacgcc ttcgtcgccg tggacgccaa                          760
```

<210> SEQ ID NO 22
<211> LENGTH: 252
<212> TYPE: PRT
<213> ORGANISM: Acetobacter sp. ATCC 15164

<400> SEQUENCE: 22

```
Arg Asp Asn Val Ser Lys Leu Arg Val Ala Trp Thr Tyr Arg Thr Gly
1               5                   10                  15

Asp Met Ala Leu Asn Gly Ala Glu Phe Gln Gly Thr Pro Ile Lys Ile
            20                  25                  30

Gly Asp Thr Val Tyr Ile Cys Ser Pro His Asn Ile Val Ser Ala Leu
        35                  40                  45

Asp Pro Asp Thr Gly Thr Glu Lys Trp Lys Phe Asp Pro His Ala Gln
    50                  55                  60

Thr Lys Val Trp Gln Arg Cys Arg Gly Val Gly Tyr Trp His Asp Ser
65                  70                  75                  80

Thr Ala Thr Asp Ala Asn Ala Pro Cys Ala Ser Arg Ile Val Leu Thr
                85                  90                  95

Thr Ile Asp Ala Arg Leu Ile Thr Ile Asp Ala Arg Thr Gly Gln Ala
            100                 105                 110

Cys Thr Asp Phe Gly Thr Asn Gly Asn Val Asn Leu Leu Thr Gly Leu
        115                 120                 125

Gly Pro Thr Ala Pro Gly Ser Tyr Tyr Pro Thr Ala Ala Pro Leu Val
    130                 135                 140

Ala Gly Asp Ile Val Val Gly Gly Arg Ile Ala Asp Asn Glu Arg
145                 150                 155                 160

Thr Gly Glu Pro Ser Gly Val Val Arg Gly Tyr Asp Val Arg Thr Gly
                165                 170                 175

Ala Gln Val Trp Ala Trp Asp Ala Thr Asn Pro His Arg Gly Thr Thr
            180                 185                 190

Pro Leu Ala Glu Gly Glu Ile Tyr Pro Ala Glu Thr Pro Asn Met Trp
        195                 200                 205

Gly Thr Ala Ser Tyr Asp Pro Lys Leu Asn Leu Val Phe Phe Pro Leu
    210                 215                 220

Gly Asn Gln Thr Pro Asp Phe Trp Gly Gly Asp Arg Ser Lys Ala Ser
225                 230                 235                 240

Asp Glu Tyr Asn Asp Ala Phe Val Ala Val Asp Ala
                245                 250
```

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23

```
ggcgcgatca tcgtggcttt                                                 20
```

```
<210> SEQ ID NO 24
<211> LENGTH: 23
<212> TYPE: DNA
<213> ORGANISM: Artificial
<220> FEATURE:
<223> OTHER INFORMATION: Primer

<400> SEQUENCE: 24
gggtcaaggg ccgagacgat gtt                                              23

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
gcacgctcga caactatgtc                                                  20

<210> SEQ ID NO 26
<211> LENGTH: 2367
<212> TYPE: DNA
<213> ORGANISM: Gluconobacter oxydans IFO 3244

<400> SEQUENCE: 26
atgaacagcg gcccccgcac gctctccatg atcatcggga ttctgggcgc cctcatggcc      60
gccttcctga tcatcgaagg cctccacctc atcatcctcg gcggctcgtg gttctacacc     120
ctcgccggca tcgcgctggc ggccagcagc gtctacatga tccgtcgcaa catcctctcg     180
acatggatcg ccctcggcct gcttgtagca acagccctgt ggtcgctcgc cgaagtcggc     240
accagcttct ggcccagctt ctcccgcctg atcgtgttcc tgtgcgtcgc cctgatcgcg     300
actctcatgg cgccctggct cagcggcccc ggccggcgct acttcacccg ccccgtcaca     360
ggggccacct ccggcgcact cggcgccatc atcgtggctt tcctcgccgg catgttccgg     420
gtccacccga ccatcgcccc gcaggacacc acccacccgc aggaaaccgc gtccaccgcc     480
gactccgacc agcccggcca tgactggccc gcctatggcc gcacagcttc cggcacgcgc     540
tacgccagct tcacacagat caaccgcgac aatgtcagca agctccgcgt cgcctggacc     600
taccgcaccg gcgacatggc gctgaacggc gccgaattcc agggcacccc catcaagatc     660
ggcgatacgg tctatatctg ctcaccccac aacatcgtct cggccctcga ccccgacacc     720
ggcacggaaa gtggaagtt cgaccccac gcccagacga agtctggca gcgctgccgc       780 ggcgtcggct actggcatga cagcacagcg acggacgcca acgcgccctg cgcctcgcgc     840
atcgtcctca ccacgatcga cgcccgcctc atcaccatcg acgcccgcac ggccaggcc     900 tgcacggatt cggaacgaa cggcaacgtc aatctcctga ccggcctcgg cccgacagcc     960
cccggctcct actacccgac cgccgccccc tcgtggcgg gtgacatcgt ggtcgtcggc    1020
ggccgcatcg ccgataacga gcgcacaggc gagccttccg gcgtcgtccg cggctacgac    1080
gtccgcaccg gcgcacaggt ctgggcctgg gacgccacca acccgcatcg cggcaccaca    1140
ccactggccg aaggcgagat ctaccccgcc gaaaccccca catgtgggg caccgccagc    1200 tacgacccga aactcaacct cgtcttcttc ccgtcggca accagacccc cgatttctgg    1260
ggcggcgacc gcagcaaggc ctcggatgaa tacaacgacg ccttcgtcgc cgtggacgcc    1320
aaaaccggcg acgaacgctg gcacttccgc accgccaacc acgatctcgt ggactacgat    1380
gccacggccc agcccatcct ctacgacatt ccggacggcc atggcggcac ccgcccggcg    1440
```

-continued

```
atcatcgcca tgaccaagcg cggccagatc ttcgtgctcg accgccgcga cggcaccccg    1500
atcgtccccg tggaaatgcg caaagtcccc caggacggcg caccggaaca ccagtacctc    1560
gcccccgaac agcccctattc cgccctctcc atcggaacag agcgcctgaa acccagcgat    1620
atgtggggcg gcacgatctt cgaccagctc ctgtgccgca tccagttcgc ctcctaccgc    1680
tatgaaggcg agttcacccc cgtcaacgag aagcaggcca ccatcatcta tccgggctat    1740
tacggcggca tcaactgggg cggcggcgcc gtggatgaaa gcaccggaac gctgctggtc    1800
aacgacatcc gcatggccca gtggggcaag ttcatgaagc aagaagaagc ccgccgcagc    1860
ggcttcaaac ccagctcgga aggcgaatat tccgaacaga aaggcacccc ctggggcgtc    1920
gtccgctcga tgttcttctc ccccgccggt ctccccctgcg tgaaaccgcc ctatggcacg    1980
atgaacgcca tcgacctgcg cagcggcaag gtcaaatgga gcatgccgct ggcacgatc    2040 caggacatgc cggtccacgg catggtcccc ggcctcgcca tcccgctcgg aatgccgacc    2100
atgagcggcc cgctggccac ccataccggc ctggtcttct tctccggcac gctcgacaac    2160
tatgtccgcg cgctcaacac cgacaccggc gaagtcgtct ggaaagcccg tctccccgtc    2220
gcctcacagg ccgctccgat gagctacatg tccgacaaga ccggcaaaca gtacatcgtc    2280
gtcaccgcag gcggcctgac ccgctccggc gtcgacaaaa accgcggcga ctacgtcatc    2340
gcctacgccc tgccctccga agaataa                                        2367
```

<210> SEQ ID NO 27
<211> LENGTH: 788
<212> TYPE: PRT
<213> ORGANISM: Gluconobacter oxydans IFO 3244

<400> SEQUENCE: 27

```
Met Asn Ser Gly Pro Arg Thr Leu Ser Met Ile Ile Gly Ile Leu Gly
1               5                   10                  15

Ala Leu Met Ala Ala Phe Leu Ile Ile Glu Gly Leu His Ile Ile
            20                  25                  30

Leu Gly Gly Ser Trp Phe Tyr Thr Leu Ala Gly Ile Ala Leu Ala Ala
        35                  40                  45

Ser Ser Val Tyr Met Ile Arg Arg Asn Ile Leu Ser Thr Trp Ile Ala
    50                  55                  60

Leu Gly Leu Leu Val Ala Thr Ala Leu Trp Ser Leu Ala Glu Val Gly
65                  70                  75                  80

Thr Ser Phe Trp Pro Ser Phe Ser Arg Leu Ile Val Phe Leu Cys Val
                85                  90                  95

Ala Leu Ile Ala Thr Leu Met Ala Pro Trp Leu Ser Gly Pro Gly Arg
            100                 105                 110

Arg Tyr Phe Thr Arg Pro Val Thr Gly Ala Thr Ser Gly Ala Leu Gly
        115                 120                 125

Ala Ile Ile Val Ala Phe Leu Ala Gly Met Phe Arg Val His Pro Thr
    130                 135                 140

Ile Ala Pro Gln Asp Thr Thr His Pro Gln Glu Thr Ala Ser Thr Ala
145                 150                 155                 160

Asp Ser Asp Gln Pro Gly His Asp Trp Pro Ala Tyr Gly Arg Thr Ala
                165                 170                 175

Ser Gly Thr Arg Tyr Ala Ser Phe Thr Gln Ile Asn Arg Asp Asn Val
            180                 185                 190

Ser Lys Leu Arg Val Ala Trp Thr Tyr Arg Thr Gly Asp Met Ala Leu
        195                 200                 205
```

```
Asn Gly Ala Glu Phe Gln Gly Thr Pro Ile Lys Ile Gly Asp Thr Val
    210                 215                 220

Tyr Ile Cys Ser Pro His Asn Ile Val Ser Ala Leu Asp Pro Asp Thr
225                 230                 235                 240

Gly Thr Glu Lys Trp Lys Phe Asp Pro His Ala Gln Thr Lys Val Trp
                245                 250                 255

Gln Arg Cys Arg Gly Val Gly Tyr Trp His Asp Ser Thr Ala Thr Asp
                260                 265                 270

Ala Asn Ala Pro Cys Ala Ser Arg Ile Val Leu Thr Thr Ile Asp Ala
            275                 280                 285

Arg Leu Ile Thr Ile Asp Ala Arg Thr Gly Gln Ala Cys Thr Asp Phe
        290                 295                 300

Gly Thr Asn Gly Asn Val Asn Leu Leu Thr Gly Leu Gly Pro Thr Ala
305                 310                 315                 320

Pro Gly Ser Tyr Tyr Pro Thr Ala Ala Pro Leu Val Ala Gly Asp Ile
                325                 330                 335

Val Val Val Gly Gly Arg Ile Ala Asp Asn Glu Arg Thr Gly Glu Pro
            340                 345                 350

Ser Gly Val Val Arg Gly Tyr Asp Val Arg Thr Gly Ala Gln Val Trp
        355                 360                 365

Ala Trp Asp Ala Thr Asn Pro His Arg Gly Thr Thr Pro Leu Ala Glu
    370                 375                 380

Gly Glu Ile Tyr Pro Ala Glu Thr Pro Asn Met Trp Gly Thr Ala Ser
385                 390                 395                 400

Tyr Asp Pro Lys Leu Asn Leu Val Phe Phe Pro Leu Gly Asn Gln Thr
                405                 410                 415

Pro Asp Phe Trp Gly Gly Asp Arg Ser Lys Ala Ser Asp Glu Tyr Asn
            420                 425                 430

Asp Ala Phe Val Ala Val Asp Ala Lys Thr Gly Asp Glu Arg Trp His
        435                 440                 445

Phe Arg Thr Ala Asn His Asp Leu Val Asp Tyr Asp Ala Thr Ala Gln
    450                 455                 460

Pro Ile Leu Tyr Asp Ile Pro Asp Gly His Gly Gly Thr Arg Pro Ala
465                 470                 475                 480

Ile Ile Ala Met Thr Lys Arg Gly Gln Ile Phe Val Leu Asp Arg Arg
                485                 490                 495

Asp Gly Thr Pro Ile Val Pro Val Glu Met Arg Lys Val Pro Gln Asp
            500                 505                 510

Gly Ala Pro Glu His Gln Tyr Leu Ala Pro Glu Gln Pro Tyr Ser Ala
        515                 520                 525

Leu Ser Ile Gly Thr Glu Arg Leu Lys Pro Ser Asp Met Trp Gly Gly
    530                 535                 540

Thr Ile Phe Asp Gln Leu Leu Cys Arg Ile Gln Phe Ala Ser Tyr Arg
545                 550                 555                 560

Tyr Glu Gly Glu Phe Thr Pro Val Asn Glu Lys Gln Ala Thr Ile Ile
                565                 570                 575

Tyr Pro Gly Tyr Tyr Gly Gly Ile Asn Trp Gly Gly Ala Val Asp
            580                 585                 590

Glu Ser Thr Gly Thr Leu Leu Val Asn Asp Ile Arg Met Ala Gln Trp
        595                 600                 605

Gly Lys Phe Met Lys Gln Glu Glu Ala Arg Arg Ser Gly Phe Lys Pro
    610                 615                 620
```

```
Ser Ser Glu Gly Glu Tyr Ser Glu Gln Lys Gly Thr Pro Trp Gly Val
625                 630                 635                 640

Val Arg Ser Met Phe Phe Ser Pro Ala Gly Leu Pro Cys Val Lys Pro
            645                 650                 655

Pro Tyr Gly Thr Met Asn Ala Ile Asp Leu Arg Ser Gly Lys Val Lys
        660                 665                 670

Trp Ser Met Pro Leu Gly Thr Ile Gln Asp Met Pro Val His Gly Met
    675                 680                 685

Val Pro Gly Leu Ala Ile Pro Leu Gly Met Pro Thr Met Ser Gly Pro
690                 695                 700

Leu Ala Thr His Thr Gly Leu Val Phe Phe Ser Gly Thr Leu Asp Asn
705                 710                 715                 720

Tyr Val Arg Ala Leu Asn Thr Asp Thr Gly Glu Val Val Trp Lys Ala
            725                 730                 735

Arg Leu Pro Val Ala Ser Gln Ala Pro Met Ser Tyr Met Ser Asp
        740                 745                 750

Lys Thr Gly Lys Gln Tyr Ile Val Val Thr Ala Gly Gly Leu Thr Arg
    755                 760                 765

Ser Gly Val Asp Lys Asn Arg Gly Asp Tyr Val Ile Ala Tyr Ala Leu
770                 775                 780

Pro Ser Glu Glu
785

<210> SEQ ID NO 28
<211> LENGTH: 30
<212> TYPE: DNA
<213> ORGANISM: Artificial
<220> FEATURE:
<223> OTHER INFORMATION: Primer

<400> SEQUENCE: 28
ccgaattcag gccgaacagc agcaggtcac                                         30

<210> SEQ ID NO 29
<211> LENGTH: 30
<212> TYPE: DNA
<213> ORGANISM: Artificial
<220> FEATURE:
<223> OTHER INFORMATION: Primer

<400> SEQUENCE: 29
gtgcctgggt acctcggtgg aggtcatgaa                                         30

<210> SEQ ID NO 30
<211> LENGTH: 30
<212> TYPE: DNA
<213> ORGANISM: Artificial
<220> FEATURE:
<223> OTHER INFORMATION: Primer

<400> SEQUENCE: 30
aagtcatatg aacagcggcc cccgcacgct                                         30

<210> SEQ ID NO 31
<211> LENGTH: 30
<212> TYPE: DNA
<213> ORGANISM: Artificial
<220> FEATURE:
```

```
<223> OTHER INFORMATION: Primer

<400> SEQUENCE: 31
atctcgagtt cttcggaggg cagggcgtag                                              30
```